(12) United States Patent
Benhabbour et al.

(10) Patent No.: US 12,377,149 B2
(45) Date of Patent: Aug. 5, 2025

(54) INJECTABLE THERMORESPONSIVE HYDROGELS AS A COMBINATORY MODALITY FOR CONTROLLED DRUG DELIVERY, BIOMATERIAL IMPLANT AND 3D PRINTING BIOINK

(71) Applicant: The University of North Carolina at Chapel Hill, Chapel Hill, NC (US)

(72) Inventors: Soumya Rahima Benhabbour, Chapel Hill, NC (US); Panita Maturavongsadit, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 17/059,790

(22) PCT Filed: May 30, 2019

(86) PCT No.: PCT/US2019/034492
§ 371 (c)(1),
(2) Date: Nov. 30, 2020

(87) PCT Pub. No.: WO2019/232114
PCT Pub. Date: Dec. 5, 2019

(65) Prior Publication Data
US 2021/0205459 A1 Jul. 8, 2021

Related U.S. Application Data

(60) Provisional application No. 62/679,334, filed on Jun. 1, 2018.

(51) Int. Cl.
| | | |
|---|---|---|
| A61K 47/38 | (2006.01) | |
| A61K 9/00 | (2006.01) | |
| A61K 31/4164 | (2006.01) | |
| A61K 31/4178 | (2006.01) | |
| A61K 31/663 | (2006.01) | |
| A61K 35/12 | (2015.01) | |
| A61K 38/00 | (2006.01) | |
| A61K 47/02 | (2006.01) | |
| A61K 47/10 | (2017.01) | |
| A61K 47/24 | (2006.01) | |
| A61K 47/26 | (2006.01) | |
| A61K 47/36 | (2006.01) | |
| A61P 19/08 | (2006.01) | |
| A61P 19/10 | (2006.01) | |
| A61P 31/00 | (2006.01) | |
| A61P 35/00 | (2006.01) | |
| B33Y 80/00 | (2015.01) | |

(52) U.S. Cl.
CPC ........... *A61K 47/38* (2013.01); *A61K 9/0019* (2013.01); *A61K 9/0024* (2013.01); *A61K 31/4164* (2013.01); *A61K 31/4178* (2013.01); *A61K 31/663* (2013.01); *A61K 35/12* (2013.01); *A61K 47/02* (2013.01); *A61K 47/10* (2013.01); *A61K 47/24* (2013.01); *A61K 47/26* (2013.01); *A61K 47/36* (2013.01); *A61P 19/08* (2013.01); *A61P 19/10* (2018.01); *A61P 31/00* (2018.01); *A61P 35/00* (2018.01); *B33Y 80/00* (2014.12); *A61K 2035/124* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 2011/0104230 | A1* | 5/2011 | Mousa | A61P 19/10 424/423 |
| 2012/0082705 | A1* | 4/2012 | Garigapati | A61L 24/02 424/602 |
| 2013/0039990 | A1 | 2/2013 | Xu et al. | |
| 2019/0015550 | A1* | 1/2019 | Lee | A61L 27/52 |
| 2021/0069378 | A1* | 3/2021 | Nelson | A61L 27/56 |

FOREIGN PATENT DOCUMENTS

| | | | | | |
|---|---|---|---|---|---|
| WO | WO-0064516 | A1 * | 11/2000 | ........... | A61K 31/663 |
| WO | WO-02098307 | A1 * | 12/2002 | ........... | A61B 17/866 |
| WO | WO 2008/059059 | A1 | 5/2008 | | |
| WO | WO 2015/036410 | A1 | 3/2015 | | |

OTHER PUBLICATIONS

Couto et al ("Development of bioactive and biodegradable chitosan-based injectable systems containing bioactive glass nanoparticles", Acta Biomaterialia, vol. 5 (2009), p. 115-123). (Year: 2009).*
Hodsman et al ("Parathyroid Hormone and Teriparatide for the Treatment of Osteoporosis: A Review of the Evidence and Suggested Guidelines for Its Use", Endocrine Reviews, vol. 26(5), p. 688-703 (2005)) (Year: 2005).*
Szymanska et al ("Influence of Unmodified and Beta-Glycerophosphate Cross-Linked Chitosan on Anti-Candida Activity of Clotrimazole in Semi-Solid Delivery Systems", Int. J. Mol. Sci. (2014), vol. 15, p. 17765-17777) (Year: 2014).*

(Continued)

*Primary Examiner* — Sin J Lee
(74) *Attorney, Agent, or Firm* — KDW FIRM PLLC

(57) ABSTRACT

Provided herein are pharmaceutical compositions that include a pharmaceutically active agent, a cellulose nanocrystal or a cellulose nanofiber, a thermogelling biocompatible polymer, and a gelling agent. Such pharmaceutical compositions can be configured as a bioink suitable for 3D printing. Such pharmaceutical compositions are suitable for treating bone disorders, including osteoporosis. Methods of treating Paget's disease, treating or preventing cancer, treating or preventing an infectious disease, and treating or preventing a disorder through regenerative medicine are also provided.

17 Claims, 15 Drawing Sheets

(56) References Cited

OTHER PUBLICATIONS

Su et al ("Osteoblastic differentiation of stem cells from human exfoliated deciduous teeth induced by thermosensitive hydrogels with strontium phosphate", Materials Science and Engineering C, vol. 52 (2015), p. 46-53) (Year: 2015).*

Wassen et al ("Effects of bisphonates on osteoblast differentiation in vitro", 52nd Annual Meeting of the Orthopaedic Research Society, Paper No. 1639, Mar. 18-22, 2006) (Year: 2006).*

Wimalawansa et al (Abstract for "Pamidronate is effective for Paget's disease of bone refractory to conventional therapy", Calcif Tissue Int. vol. 53(4) (Oct. 1993), p. 237-41). (Year: 1993).*

Brixen et al (Abstract for "Teriparatide (biosynthetic human parathyroid hormone 1-34): a new paradigm in the treatment of osteoporosis", Basic Clin Pharmacol Toxicol. vol. 94(6) (Jun. 2004), p. 260-70). (Year: 2004).*

Andani, M. T.; Shayesteh Moghaddam, N.; Haberland, C.; Dean, D.; Miller, M. J.; Elahinia, M. Metals for Bone Implants. Part 1. Powder Metallurgy and Implant Rendering. Acta Biomater 2014, 10, 4058-4070.

Bae, J.; Park, J. W. Preparation of an Injectable Depot System for Long-Term Delivery of Alendronate and Evaluation of Its Anti-Osteoporotic Effect in an Ovariectomized Rat Model. Int. J. Pharm. 2015, 480, 37-47.

Black, D. M.; Delmas, P. D.; Eastell, R.; Reid, I. R.; Boonen, S.; Cauley, J. A.; Cosman, F.; Lakatos, P.; Leung, P. C.; Man, Z.; Mautalen, C.; Mesenbrink, P.; Hu, H.; Caminis, J.; Tong, K.; Rosario-Jansen, T.; Krasnow, J.; Hue, T. F.; Sellmeyer, D.; Eriksen, E. F.; Cummings, S. R. Once-Yearly Zoledronic Acid for Treatment of Postmenopausal Osteoporosis. N. Engl. J. Med. 2007, 356, 1809-1822.

Burg, K. J.; Porter, S.; Kellam, J. F. Biomaterial Developments for Bone Tissue Engineering. Biomaterials 2000, 21, 2347-2359.

Cha, C.; Shin, S. R.; Gao, X.; Annabi, N.; Dokmeci, M. R.; Tang, X. S.; Khademhosseini, A. Controlling Mechanical Properties of Cell-Laden Hydrogels by Covalent Incorporation of Graphene Oxide. Small (Weinheim an der Bergstrasse, Germany) 2014, 10, 514-523.

Cosman, F.; de Beur, S. J.; LeBoff, M. S.; Lewiecki, E. M.; Tanner, B.; Randall, S.; Lindsay, R. Clinician's Guide to Prevention and Treatment of Osteoporosis. Osteoporos. Int. 2014, 25, 2359-2381.

Cramer, J. A.; Gold, D. T.; Silverman, S. L.; Lewiecki, E. M. A Systematic Review of Persistence and Compliance with Bisphosphonates for Osteoporosis. Osteoporos. Int. 2007, 18, 1023-1031.

De France, K. J.; Chan, K. J.; Cranston, E. D.; Hoare, T. Enhanced Mechanical Properties in Cellulose Nanocrystal-Poly(Oligoethylene Glycol Methacrylate) Injectable Nanocomposite Hydrogels through Control of Physical and Chemical Cross-Linking. Biomacromolecules 2016, 17, 649-660.

Ezzati Nazhad Dolatabadi, J.; Hamishehkar, H.; Valizadeh, H. Development of Dry Powder Inhaler Formulation Loaded with Alendronate Solid Lipid Nanoparticles: Solid-State Characterization and Aerosol Dispersion Performance. Drug Dev. Ind. Pharm. 2015, 41, 1431-1437.

In Bone Health and Osteoporosis: A Report of the Surgeon General, Rockville (MD), 2004.

International Preliminary Report on Patentability corresponding to International Application No. PCT/US2019/034492 dated Dec. 1, 2020.

International Search Report corresponding to International Application No. PCT/US2019/034492 dated Sep. 19, 2019.

Jeremiah et al., "Diagnosis and Management of Osteoporosis." American Academy of Family Physicians, vol. 92(4), pp. 261-268 (2015) https://www.aafp.org/afp/2015/0815/p261.html (Jan. 9).

Kennel, K. A.; Drake, M. T. Adverse Effects of Bisphosphonates: Implications for Osteoporosis Management. Mayo Clin. Proc. 2009, 84, 632-638.

Kwong, F. N. K.; Harris, M. B. Recent Developments in the Biology of Fracture Repair. JAAOS—Journal of the American Academy of Orthopaedic Surgeons 2008, 16, 619-625.

Maturavongsadit, P.; Bi, X.; Metavarayuth, K.; Luckanagul, J. A.; Wang, Q. Influence of Cross-Linkers on the in Vitro Chondrogenesis of Mesenchymal Stem Cells in Hyaluronic Acid Hydrogels. ACS applied materials & interfaces 2016.

Maturavongsadit, P.; Luckanagul, J. A.; Metavarayuth, K.; Zhao, X.; Chen, L.; Lin, Y.; Wang, Q. Promotion of in Vitro Chondrogenesis of Mesenchymal Stem Cells Using in Situ Hyaluronic Hydrogel Functionalized with Rod-Like Viral Nanoparticles. Biomacromolecules 2016, 17, 1930-1938.

Mikael, P. E.; Nukavarapu, S. P. Functionalized Carbon Nanotube Composite Scaffolds for Bone Tissue Engineering: Prospects and Progress. Journal of Biomaterials and Tissue Engineering 2011, 1, 76-85.

Miljanić, S.; Frkanec, L.; Biljan, T.; Meić, Z.; Žinić, M. Surface-Enhanced Raman Scattering on Colloid Gels Originated from Low Molecular Weight Gelator. Journal of Raman Spectroscopy: An International Journal for Original Work in all Aspects of Raman Spectroscopy, Including Higher Order Processes, and also Brillouin and Rayleigh Scattering 2008, 39, 1799-1804.

Murphy, W. L.; McDevitt, T. C.; Engler, A. J. Materials as Stem Cell Regulators. Nature materials 2014, 13, 547.

Orellana, B. R.; Hilt, J. Z.; Puleo, D. A. Drug Release from Calcium Sulfate-Based Composites. Journal of biomedical materials research. Part B, Applied biomaterials 2015, 103, 135-142.

Supper, S.; Anton, N.; Seidel, N.; Riemenschnitter, M.; Curdy, C.; Vandamme, T. Thermosensitive Chitosan/Glycerophosphate-Based Hydrogel and Its Derivatives in Pharmaceutical and Biomedical Applications. Expert Opin Drug Deliv 2014, 11, 249-267.

Suzuki, M.; Yumoto, M.; Shirai, H.; Hanabusa, K. Supramolecular Gels Formed by Amphiphilic Low-Molecular-Weight Gelators of Nα, Nε-Diacyl-L-Lysine Derivatives. Chemistry—A European Journal 2008, 14, 2133-2144.

Temmerman, A.; Rasmusson, L.; Kübler, A.; Thor, A.; Quirynen, M. An Open, Prospective, Non-Randomized, Controlled, Multicentre Study to Evaluate the Clinical Outcome of Implant Treatment in Women over 60 years of Age with Osteoporosis/Osteopenia: 1-Year Results. Clin. Oral Implants Res. 2017, 28, 95-102.

Written Opinion corresponding to International Application No. PCT/US2019/034492 dated Sep. 5, 2019.

You, J.; Cao, J.; Zhao, Y.; Zhang, L.; Zhou, J.; Chen, Y. Improved Mechanical Properties and Sustained Release Behavior of Cationic Cellulose Nanocrystals Reinforeced Cationic Cellulose Injectable Hydrogels. Biomacromolecules 2016, 17, 2839-2848.

* cited by examiner

| Hydrogel | Gelation time (s) at 37 °C | Complex modulus at 37 °C (kPa) |
|---|---|---|
| CS | 24 ± 17 | 28.6 ± 7.6 |
| CS+0.5%CNC | Less than 7 | 86.0 ± 10.0 |
| CS+1.0%CNC | Less than 7 | 111.0 ± 17.0 |
| CS+2.0%CNC | Less than 7 | 379.3 ± 78.2 |

| Hydrogel | Composition (%w/v) | | | | Degree of shrinkage (%w/w) | Gel fraction (%w/w) |
|---|---|---|---|---|---|---|
| | CS | HEC | BGP | CNC | | |
| CS | 2 | 0.05 | 2.16 | - | 67.99 ± 2.62 | 2.31 ± 0.05 |
| CS+0.5%CNC | 2 | 0.05 | 2.16 | 0.5 | 61.46 ± 0.68 | 2.79 ± 0.04 |
| CS+1.0%CNC | 2 | 0.05 | 2.16 | 1.0 | 61.19 ± 0.98 | 3.14 ± 0.04 |
| CS+2.0%CNC | 2 | 0.05 | 2.16 | 2.0 | 58.59 ± 2.47 | 4.09 ± 0.06 |

Fig. 3C

INJECTABLE THERMORESPONSIVE HYDROGELS AS A COMBINATORY MODALITY FOR CONTROLLED DRUG DELIVERY, BIOMATERIAL IMPLANT AND 3D PRINTING BIOINK

CROSS-REFERENCE TO RELATED APPLICATIONS

This application claims benefit of U.S. Provisional Patent Application Ser. No. 62/679,334, filed Jun. 1, 2018, herein incorporated by reference in its entirety.

TECHNICAL FIELD

The subject matter disclosed herein relates to injectable thermoresponsive hydrogels as a combinatory modality for controlled drug delivery, biomaterial implant, and 3D printing bioink.

BACKGROUND

Osteoporosis is a worldwide chronic disease associated with decreased bone strength, resulting in bone fracture which leads to high morbidity and mortality rates.[1,2] The International Osteoporosis Foundation estimates that osteoporosis affects more than 200 million people worldwide,[3] including 44 million people of age 50 and older in the United State which represents 55% of Americans in this age group.[4] Standard of care (SOC) therapies along with changes in lifestyle are primary methods for treatment of osteoporosis. However, current SOC with first-line drugs are administered daily orally or intravenously. Akin to their adverse effects and dosing frequency, poor compliance with these therapies lead to diminished medication efficacy.[5,6] Therefore, long-acting formulations for delivery of these first-line drugs would be the ideal strategy to overcome these limitations and improve therapeutic efficacy.

In the event of osteoporotic fracture, surgical procedures are required to implant biomaterials to promote fracture healing.[7] To date, the biomaterials used for osteoporosis in the market are still limited by their 1) inadequate mechanical integrity,[8,9] 2) lack of ability to support all irregular shapes of an osteoporotic fracture, and 3) in some cases, these scaffolds are made with non-biodegradable materials and require surgical removal. As a result, the fractures do not heal properly and recurrently fracture at the same sites. In this regard, biodegradable biomaterials with suitable mechanical integrity and that can be adaptable to fit specific fracture shapes are in high need and would be the ideal strategy to support and promote the healing of osteoporotic fractures.

The present disclosure overcomes previous shortcomings in the art by providing injectable thermoresponsive hydrogels as a combinatory modality for controlled drug delivery and biomaterial implant.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are pharmaceutical compositions comprising a pharmaceutically active agent, a cellulose nanocrystal or a cellulose nanofiber, a thermogelling biocompatible polymer, and a gelling agent. In some aspects, the thermogelling biocompatible polymer can be a chitosan or a chitosan derivative. In some embodiments, the gelling agent can be selected from the group consisting of β-glycerophosphate, glycerol and mannitol. In some aspects, the pharmaceutical composition further comprises a pharmaceutically acceptable carrier.

In some embodiments, such pharmaceutical compositions can further comprise at least one of, or any combination of, a compound selected from a group consisting of: inorganic phosphate salt, glycerol, mannitol, m-cresol, benzyl alcohol and other alcohol. The pharmaceutical composition can be suitable for subcutaneous, intramuscular (IM) injection, intraosseous injection, or a bioink for 3D printing. In some aspects, the pharmaceutically active agent comprises a bisphosphonate or a teriparatide, or a pharmaceutically acceptable salt of a bisphosphonate or a teriparatide. The pharmaceutically active agent can be for treating a bone disorder, optionally wherein the bone disorder is osteoporosis. In some aspects, the pharmaceutically active agent can be configured for treating Paget's disease. In some embodiments, the pharmaceutically active agent can be for treating or preventing cancer, diabetes, or an infectious disease. In some embodiments, the pharmaceutically active agent can be for treating or preventing a disorder through regenerative medicine, wherein the regenerative medicine comprises bone regeneration or tissue regeneration. In some embodiments, the pharmaceutical compositions can further comprise one or more stem cells, wherein stem cells can be encapsulated in or seeded on the thermogelling biocompatible polymer. In some aspects the stem cells can be osteoblasts for tissue engineering or neural stem cells (iNSCs) for treatment of Glioblastoma multiforme (GBM).

In some embodiments, the disclosed pharmaceutical compositions can be configured as a bioink suitable for 3D printing. The bioinks can comprises one or more of the following properties: a viscosity of less than about 800 cP, syringeability through a 16-25 gauge needle at room temperature, pH of about 6.5 to about 7.5, osmolarity of about 260 to about 400 mOsm/kg, a yield stress of less than about 600 Pa, and/or a storage modulus recovery of at least 90% from its initial storage modulus. The bioink can comprise one or more of the following properties: gelation time of less than about one minute, post-gelling compression force of about 10 to about 400 kPa, and supportive of greater than 80% cell viability.

In some embodiments, provided herein are methods of treating a bone disorder comprising administering a therapeutically effective amount of a pharmaceutical composition disclosed herein to a subject in need thereof. In such methods the administering can comprise subcutaneous, intramuscular, or intraosseous injection of the pharmaceutical composition. In some aspects, the bone disorder in such methods can be osteoporosis. The subject can be a human subject.

In some embodiments, provided herein are methods of treating or preventing Paget's disease comprising administering a therapeutically effective amount of a pharmaceutical composition as disclosed herein to a subject in need thereof. In some embodiments, provided herein are methods of treating or preventing cancer comprising administering a therapeutically effective amount of a pharmaceutical as disclosed herein to a subject in need thereof. In some embodiments, provided herein are methods of treating or preventing an infectious disease comprising administering a therapeutically effective amount of a pharmaceutical composition disclosed herein to a subject in need thereof. In some embodiments, provided herein are methods of treating or preventing a disorder through regenerative medicine comprising administering a therapeutically effective amount of a pharmaceutical composition disclosed herein to a subject in need thereof.

These and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, drawings and examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, can be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

Like numbers refer to like elements throughout. In the figures, the thickness of certain lines, layers, components, elements or features can be exaggerated for clarity. Where used, broken lines illustrate optional features or operations unless specified otherwise.

For a more complete understanding of the presently disclosed subject matter, reference is now made to the below drawings.

Figure 1A:
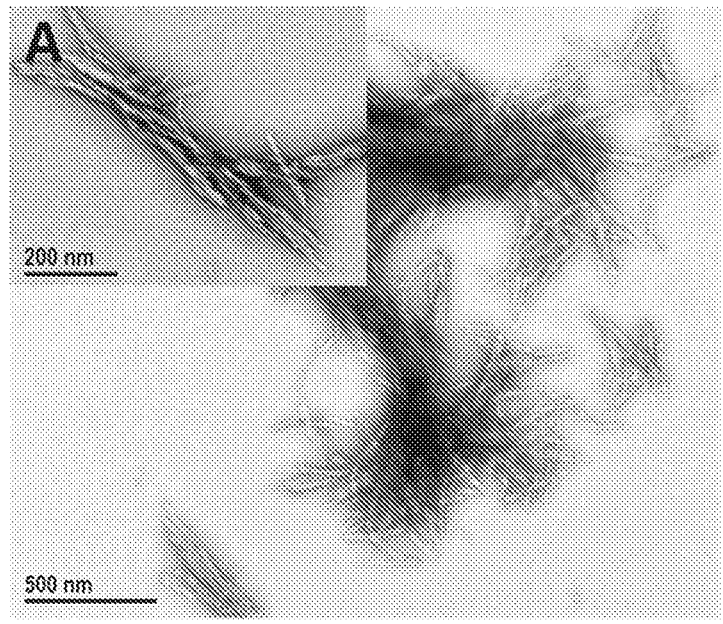
Figure 1B:
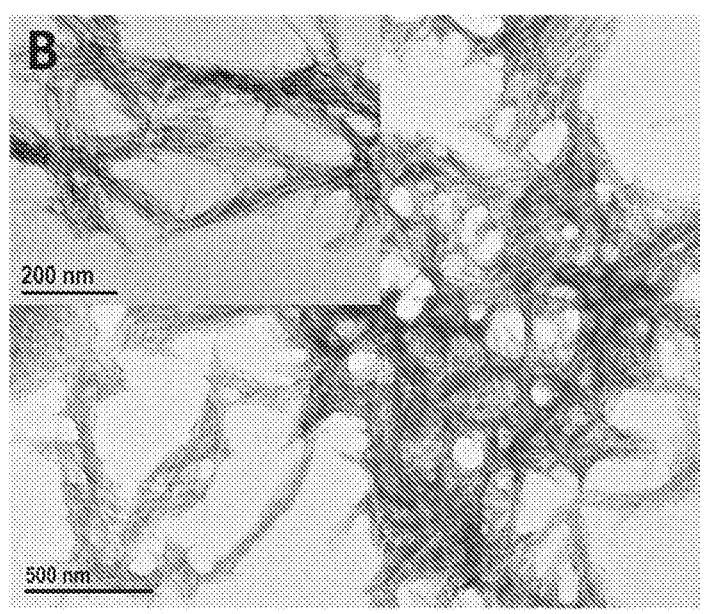

FIGS. 1A and 1B are transmission electron microscopy (TEM) images of isolated cellulose nanocrystals synthesized by 40% (v/v) sulfuric acid assisted with sonication at 45° C. for 60 min (FIG. 1A), and 50% (v/v) sulfuric acid assisted with sonication at 45° C. for 10 min (FIG. 1B).

Figure 2A:
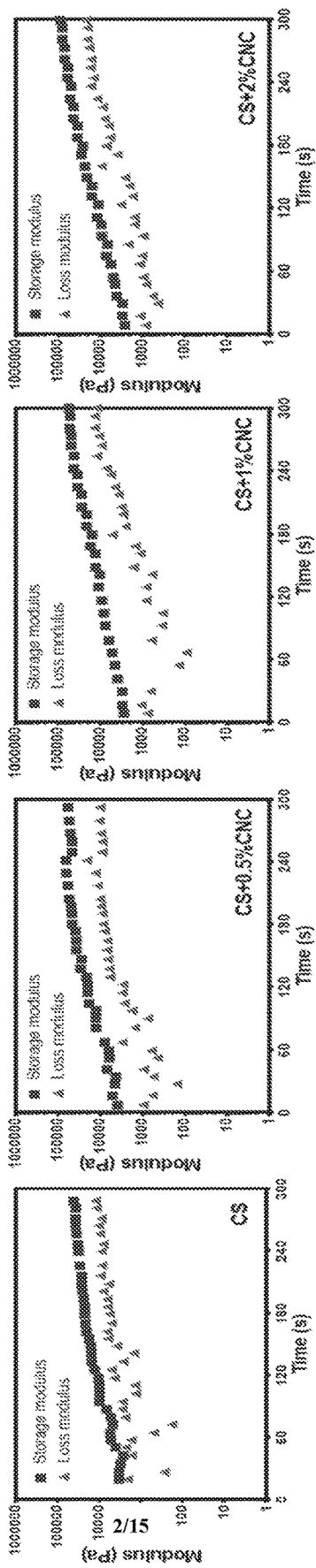
Figures 2B, 2C:
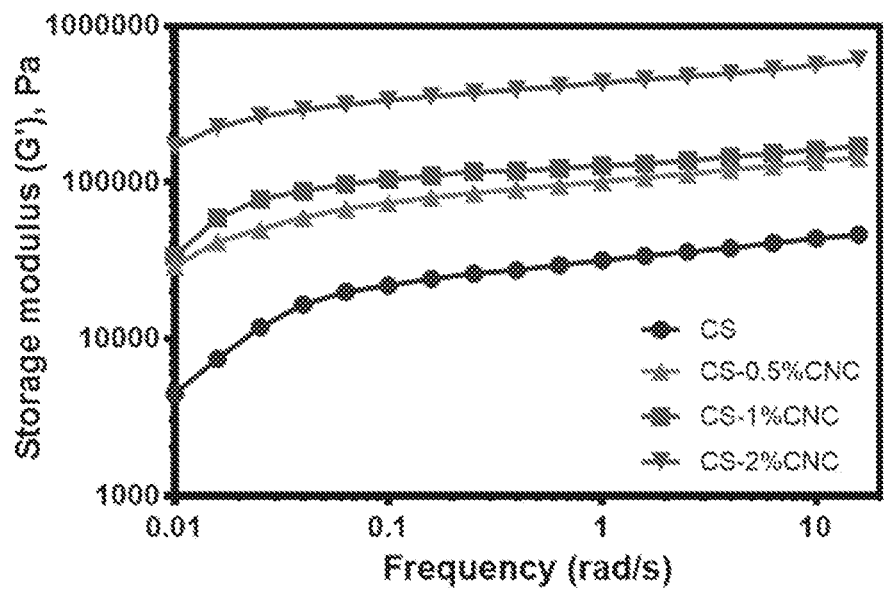

FIG. 2A shows data of gelation time of prototype injectable hydrogels (CS, CS+0.5% CNC, CS+1% CNC, and CS+2% CNC) determined by a time at crossover of storage (E') and loss modulus (E"). FIG. 2B shows data of mechanical properties of the prototype injectable hydrogels (CS, CS+0.5% CNC, CS+1% CNC, and CS+2% CNC). The elastic modulus of the hydrogels using amplitude strain at 10%, range of frequency at 0.1-15 rad/s. FIG. 2C shows the average gelation times and complex modulus of the hydrogels (n=3).

Figure 3A:
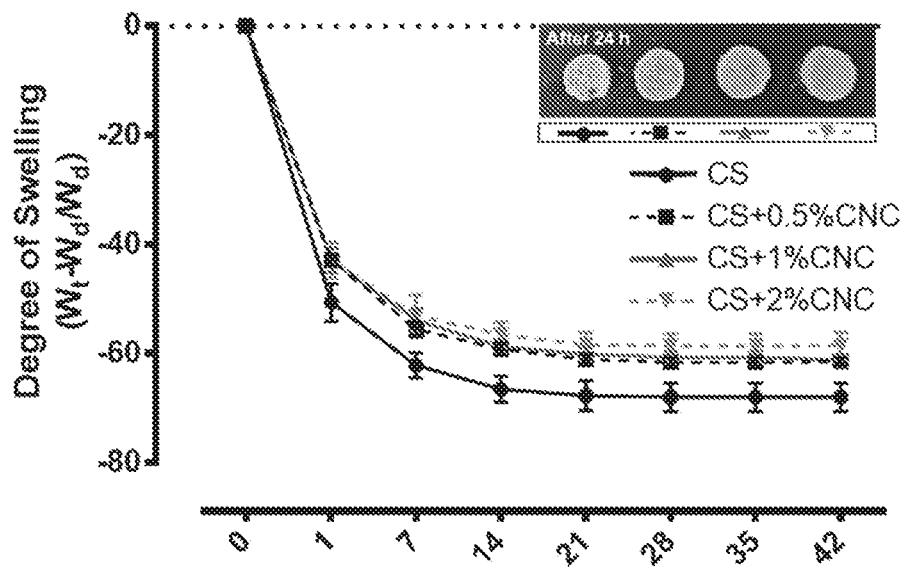
Figure 3B:
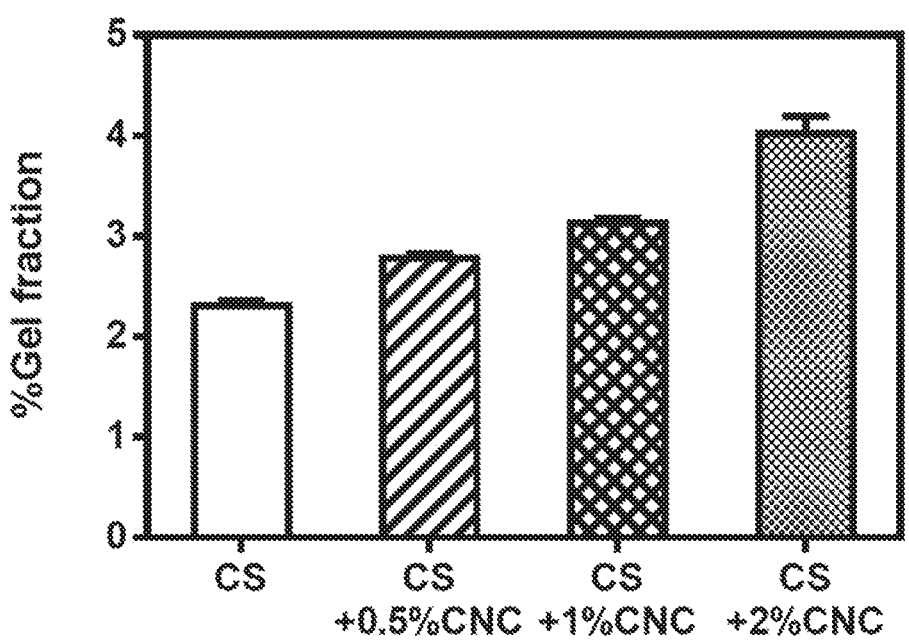
Figure 3D:
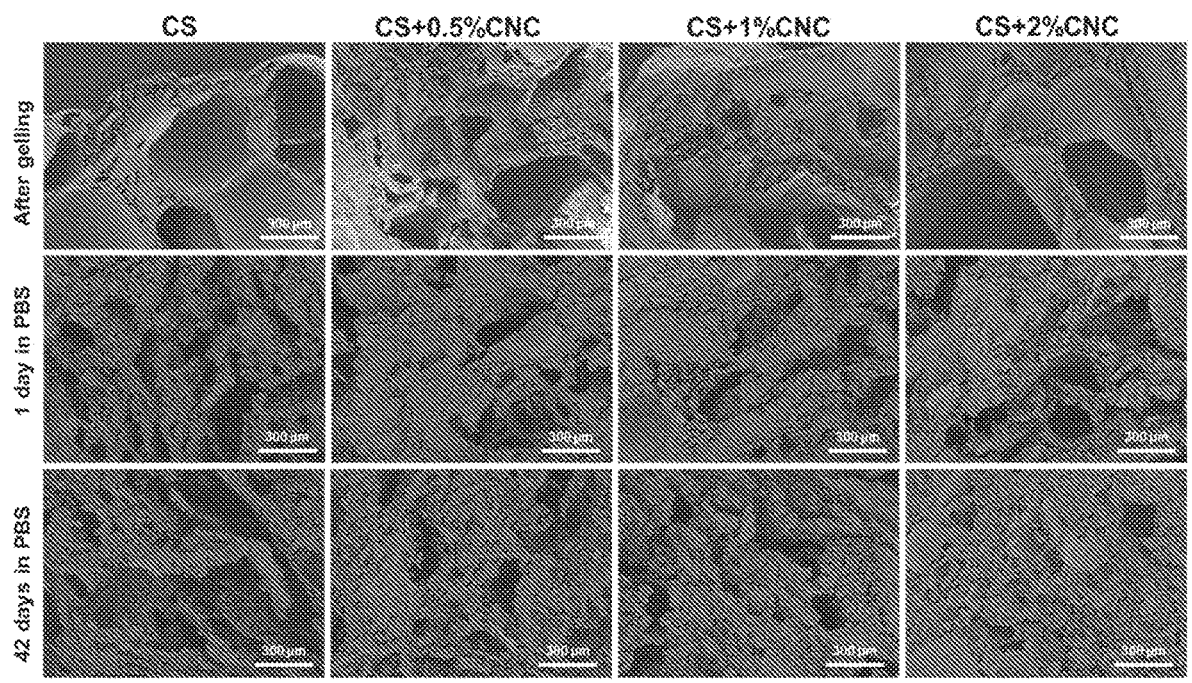

FIG. 3A is a graphical depiction of data showing the degree of swelling of prototype injectable hydrogels. Inset represents the structure of the hydrogel after incubation in PBS pH 7.4 for 24 h. FIG. 3B is shows the percent gel fraction of hydrogels after 42 days post-incubation in PBS. FIG. 3C shows data summarizing shrinkage degrees and gel fractions of prototype injectable hydrogels. FIG. 3D are images of the microstructure of hydrogels after gelling collected at 1 day, and 42 days post-incubation in PBS.

Figure 4A:
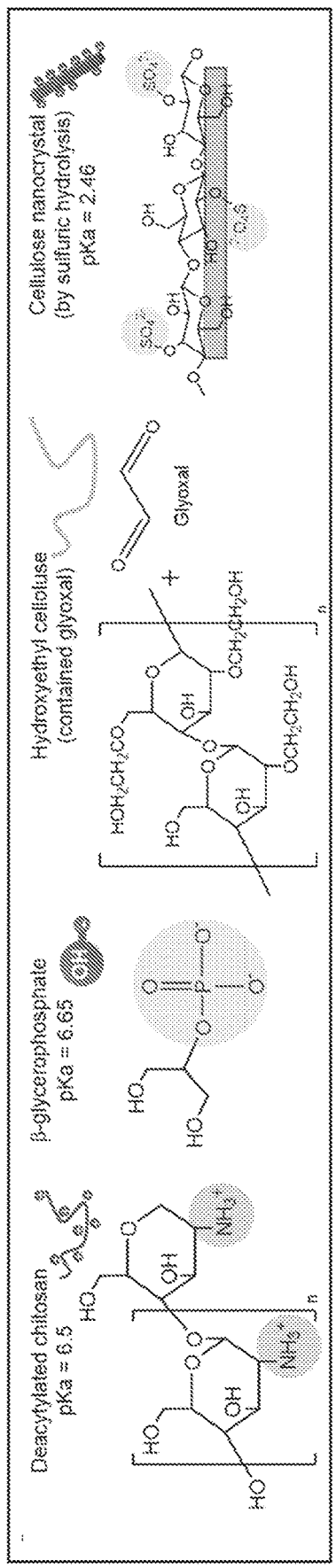
Figure 4B:
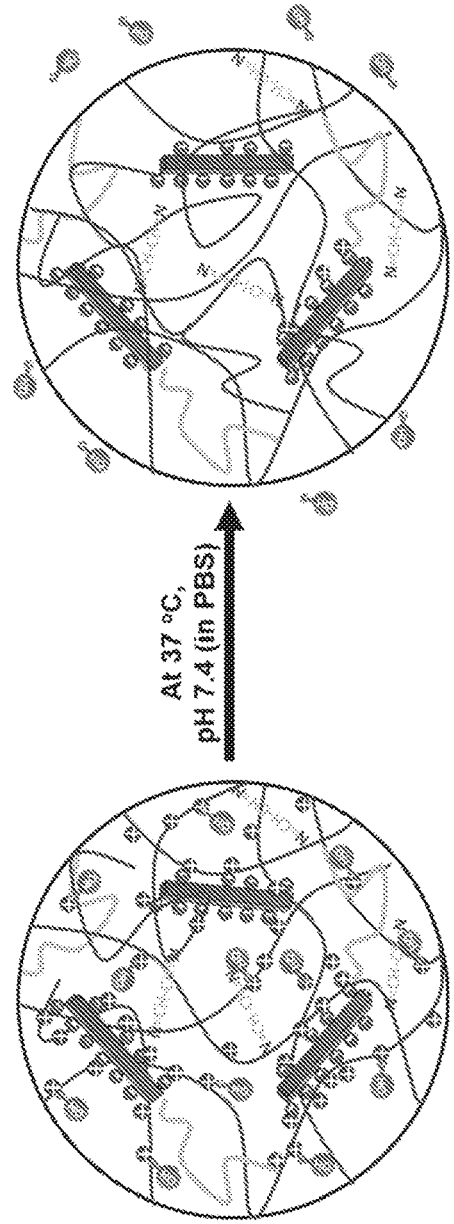
Figure 4C:
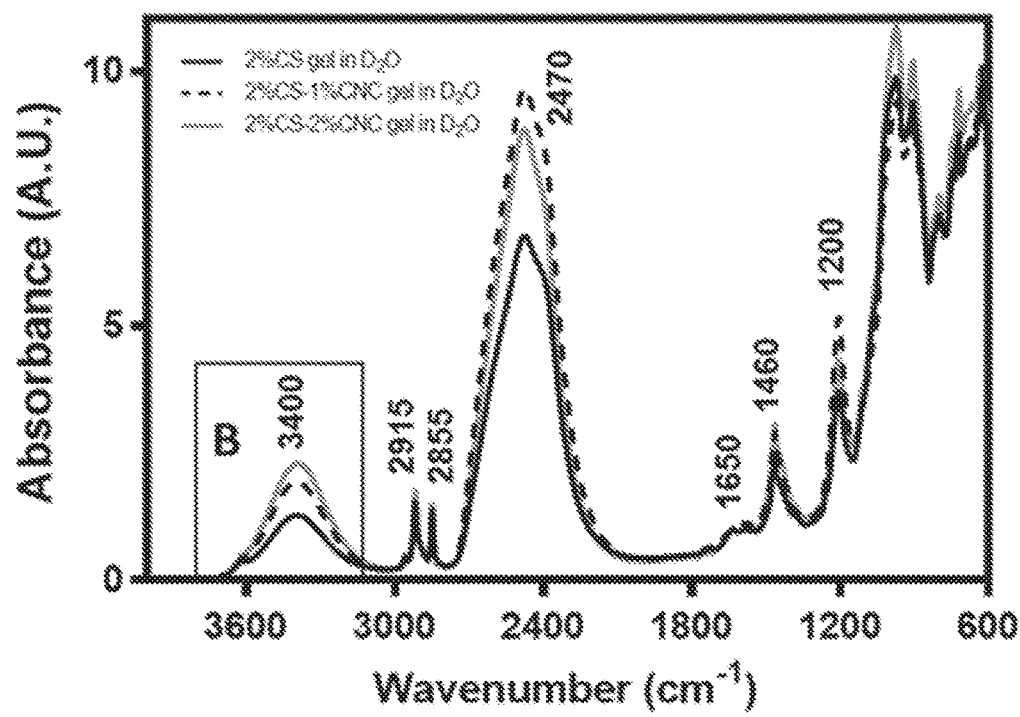
Figure 4D:
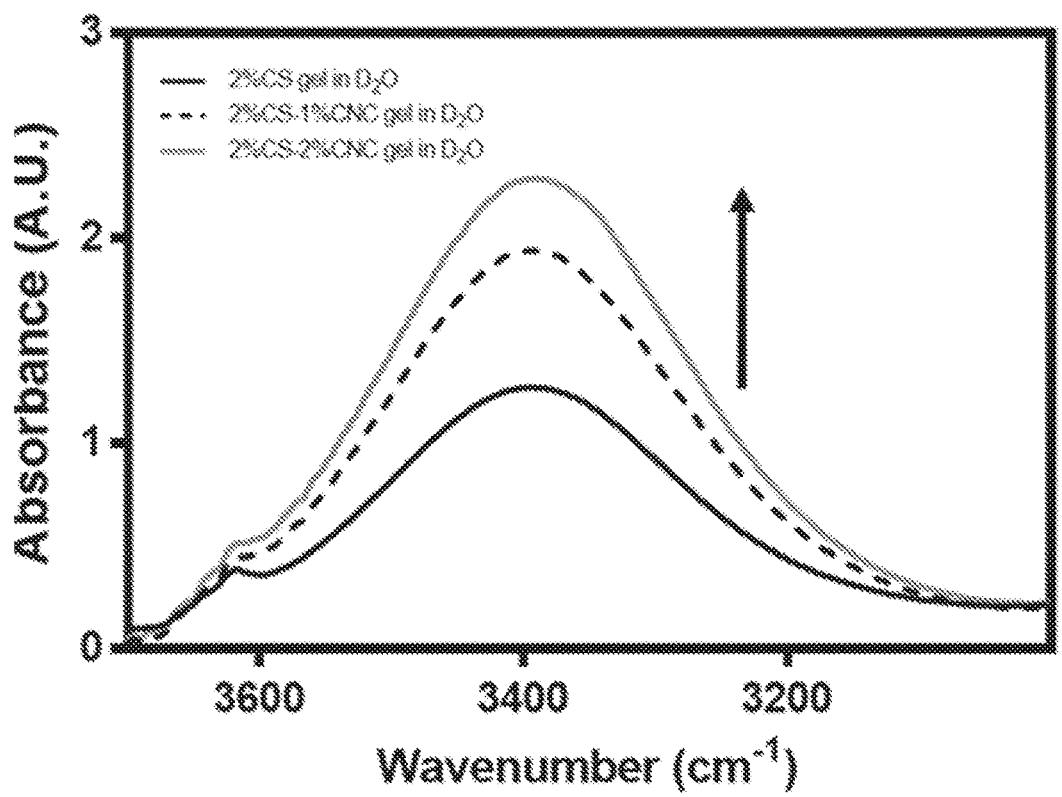
Figure 4E:
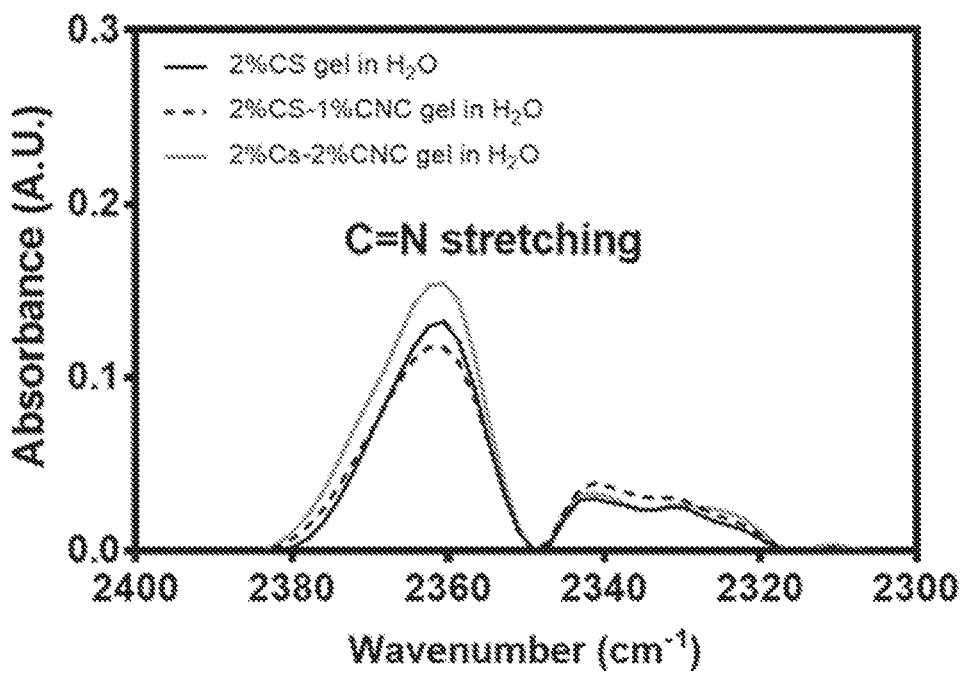

FIG. 4A is a schematic illustration of the chemical structures of hydrogel compositions disclosed herein and their pKa, including CS, BGP, HEC, and CNCs. FIG. 4B is a schematic illustration of the proposed mechanism of hydrogel formation in the CS-CNC networks. FIG. 4C is a Fourier-transform infrared spectroscopy (FTIR) spectra of different CS hydrogel formulations in deuterium dioxide. FIG. 4D is an FTIR spectra showing the increase of absorbance at 3400 $cm^{-1}$ in the CS-CNC hydrogel formulations immersed in deuterium dioxide compared to the CS hydrogel. FIG. 4E is an FTIR spectra of different CS hydrogel formulations in water showing the absorbance at 2360 $cm^{-1}$ attribute to the C=N bonding of glyoxal molecules from HEC and the amine groups of CS.

Figure 5:
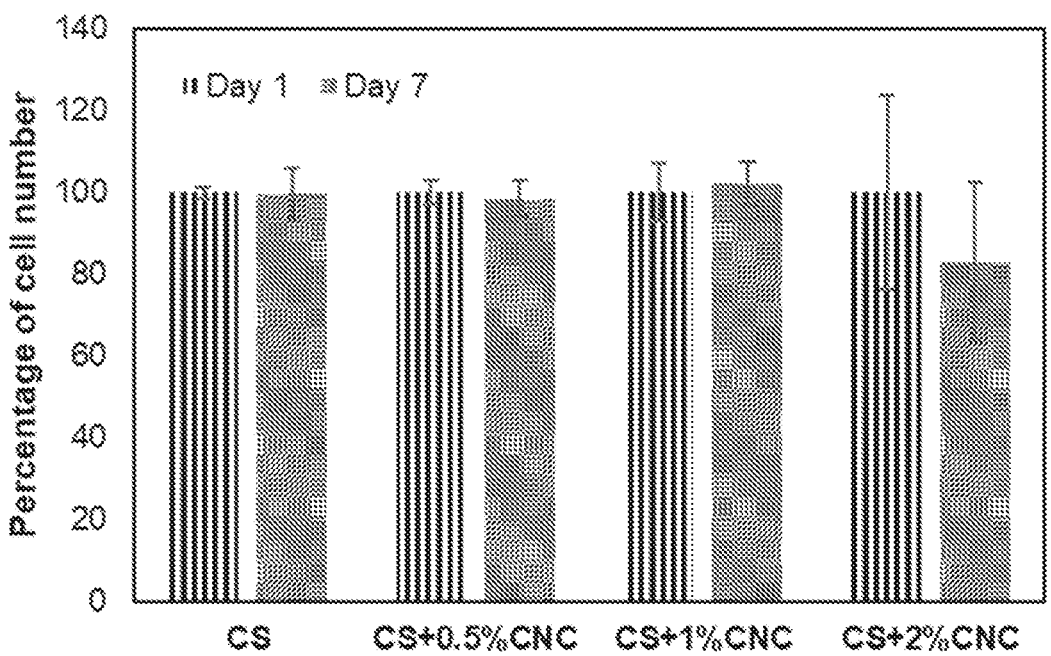

FIG. 5 is a graphical depiction of the percentage of cell proliferation on day 7 compared to day 1 in each hydrogel formulation using cell counter imageJ analysis.

Figure 6:
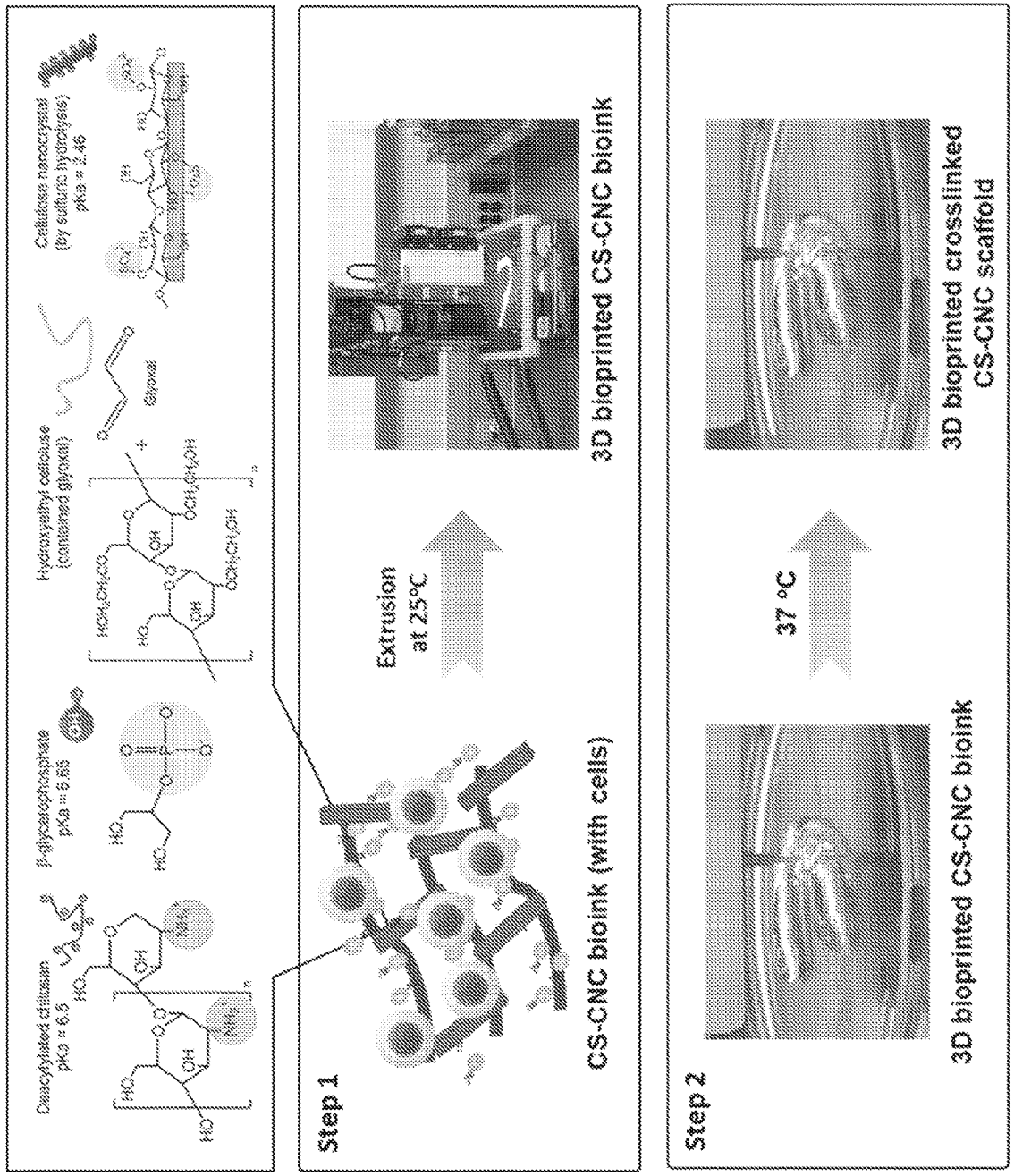

FIG. 6 is a schematic illustration of the 3D bioprinting process.

Figure 7A:
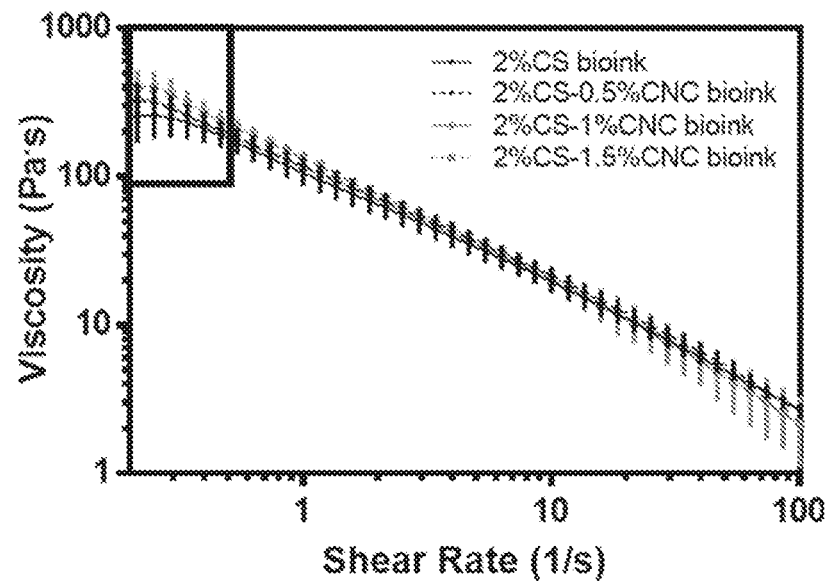
Figure 7B:
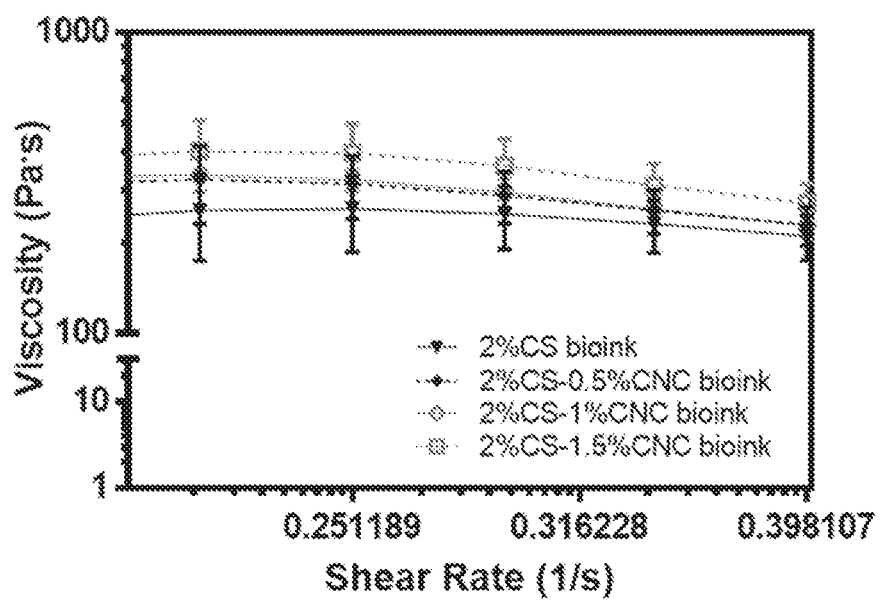
Figure 7C:
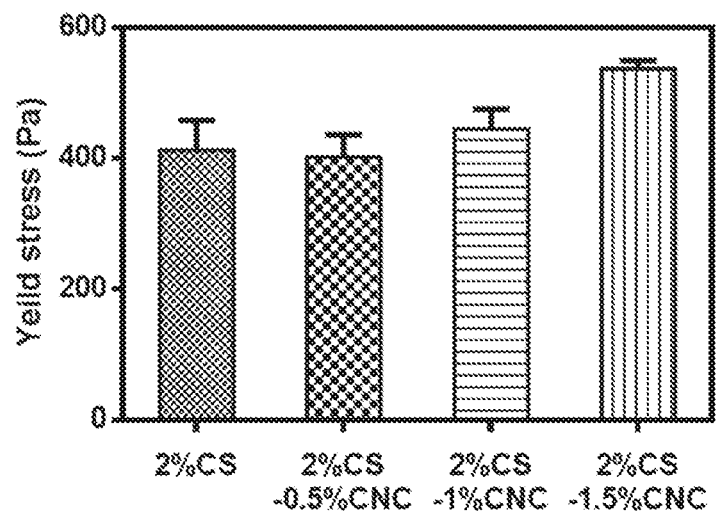
Figure 7D:
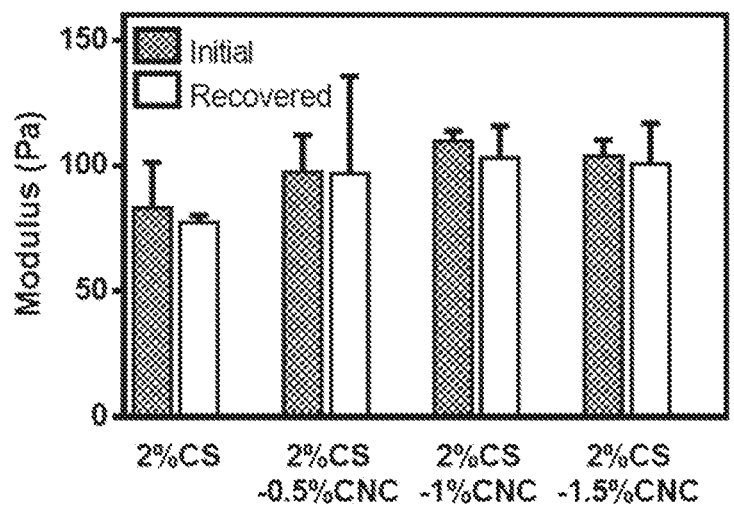

FIG. 7A shows the viscosity curve of the optimized bioinks (n=3) with different percentage of incorporated CNCs at shear rate from 0-100 $s^{-1}$. FIG. 7B shows the viscosity curve of optimized bioinks (n=3) focused at initial shear rate. FIG. 7C shows the yield stress of the optimized bioinks (n=3) determined by an oscillatory shear strain sweep from 0.1% to 200% at frequency of 1 Hz. FIG. 7D shows the storage modulus recovery of bioinks (n=3) showing the recovered storage modulus after undergoing 2000% strain (above yield stress) for 30 s compared to their initial modulus.

Figure 8A:
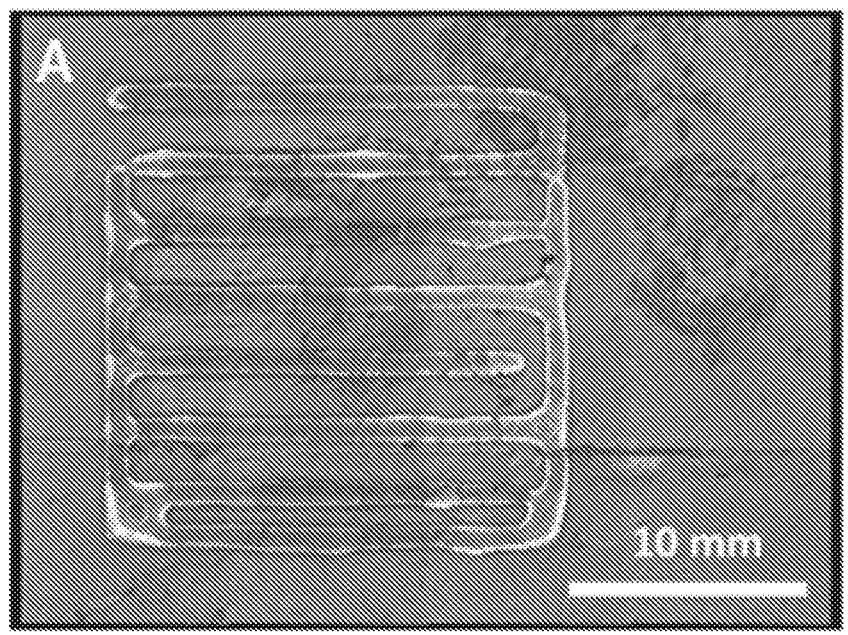
Figure 8B:
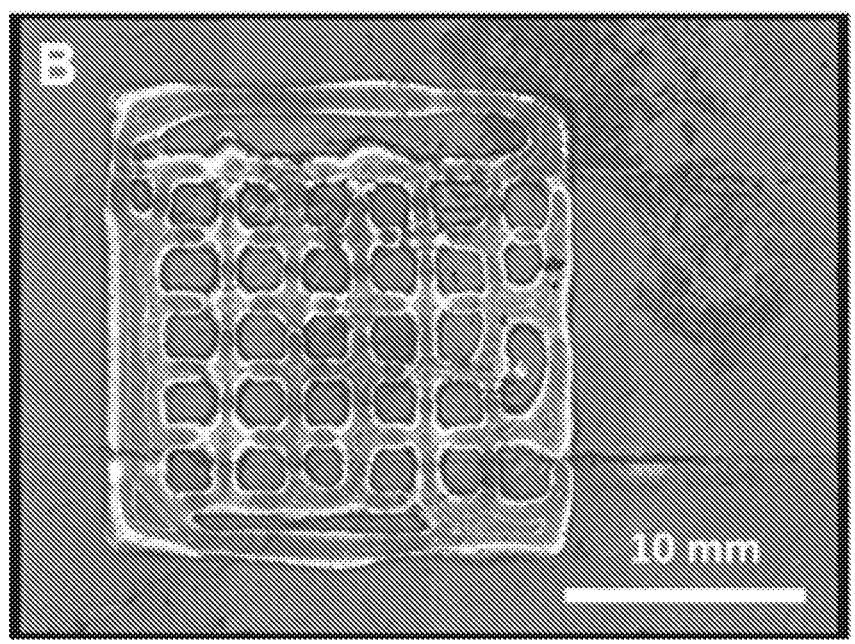
Figure 8C:
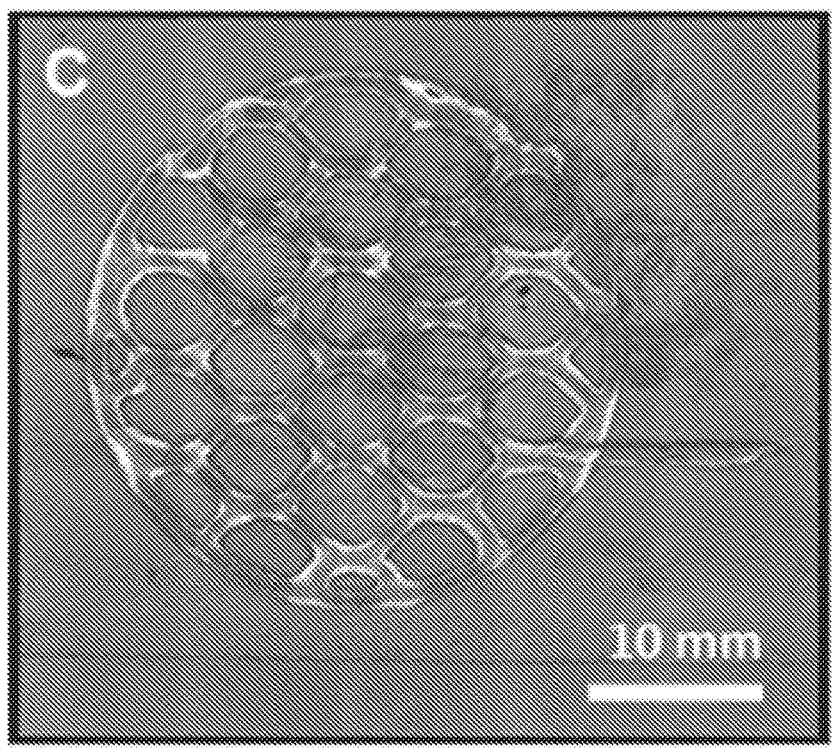
Figure 8D:
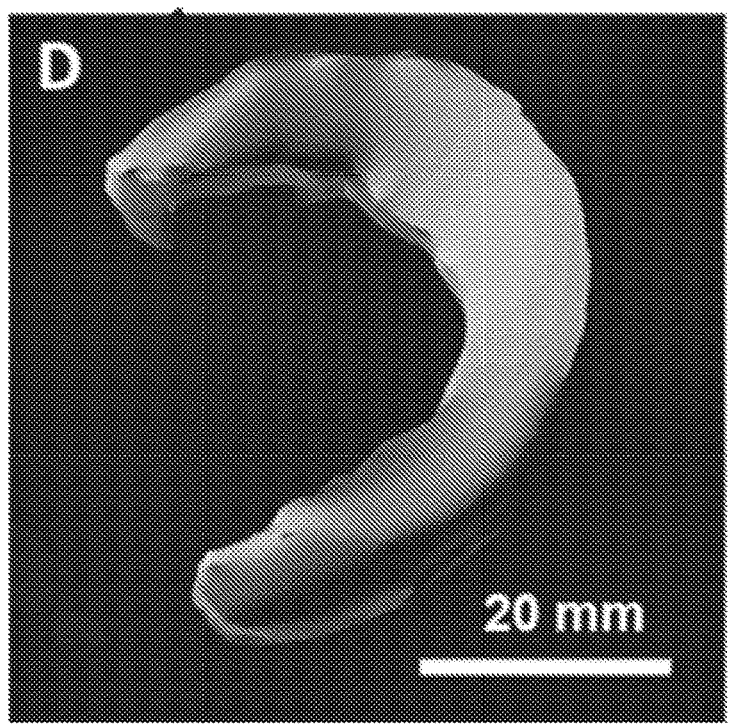
Figure 8E:
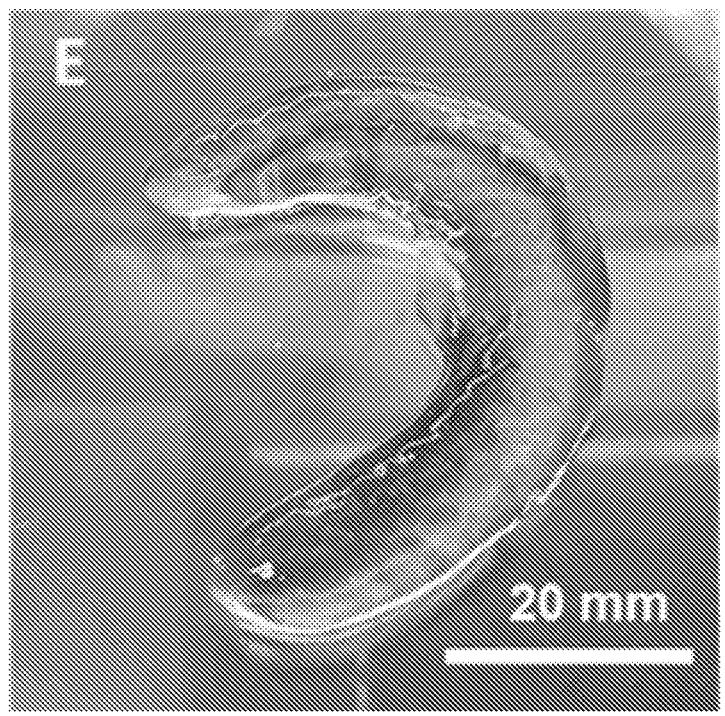

FIGS. 8A-8C are images of 3D printing of prototype CS scaffolds, with FIG. 8A showing a single-layer 20×20×5 mm straight-line structure, FIG. 8B showing a single-layer 20×20×5 mm cross-line structure, and FIG. 8C showing a single-layer 20 mm honeycomb structure. FIG. 8D is a computer aided design (CAD) knee meniscus model from a patient's MRI scan, compared to FIG. 8E showing a CNC-CS hydrogel scaffolds printed through a 3D bioprinter.

DETAILED DESCRIPTION

The presently disclosed subject matter now will be described more fully hereinafter, in which some, but not all embodiments of the presently disclosed subject matter are described. Indeed, the disclosed subject matter can be embodied in many different forms and should not be construed as limited to the embodiments set forth herein; rather, these embodiments are provided so that this disclosure will satisfy applicable legal requirements.

Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the present disclosure and the claims.

All publications, patent applications, patents and other references cited herein are incorporated by reference in their entireties for the teachings relevant to the sentence and/or paragraph in which the reference is presented.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein, the term "substantially," when referring to a value, an activity, or to an amount of a composition, mass, weight, temperature, time, volume, concentration, percentage, etc., is meant to encompass variations of in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed apparatuses and devices.

Also as used herein, the terms "treat," "treating" or "treatment" may refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the terms "prevent," "preventing" or "prevention of" (and grammatical variations thereof) may refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent", "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

An "effective amount" or "therapeutically effective amount" may refer to an amount of a compound or composition of this invention that is sufficient to produce a desired effect, which can be a therapeutic and/or beneficial effect. The effective amount will vary with the age, general condition of the subject, the severity of the condition being treated, the particular agent administered, during the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, The Science and Practice of Pharmacy (latest edition)).

Subjects suitable to be treated with the composition, compositions and formulations of the present invention include, but are not limited to mammalian subjects. Mammals according to the present invention include, but are not limited to, canines, felines, bovines, caprines, equines, ovines, porcines, rodents (e.g., rats and mice), lagomorphs, primates, humans and the like, and mammals in utero. Any mammalian subject in need of being treated or desiring treatment according to the present invention is suitable. Human subjects of any gender (for example, male, female or transgender) and at any stage of development (i.e., neonate, infant, juvenile, adolescent, adult, elderly) may be treated according to the present invention.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "prevent," as used herein, means to stop something from happening, or taking advance measures against something possible or probable from happening. In the context of medicine, "prevention" generally refers to action taken to decrease the chance of getting a disease or condition.

The term "regulate" refers to either stimulating or inhibiting a function or activity of interest.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%. The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

General Considerations

Standard of care therapies along with changes in lifestyle are primary methods for treatment of osteoporosis. Current marketed first-line medications for osteoporosis are mostly prescribed as daily or weekly administration of oral tablets or injectable solutions and have adverse side effects including difficulty swallowing, heartburn, upper gastrointestinal irritations, and flulike symptoms,[6,10] which lead to reduced efficacy of the treatment.[5,6] A number of long-acting injectable formulations for delivery of these drugs are currently in preclinical development. Examples include an intramuscular injection of alendronate-loaded PLGA microparticles, an intraosseous injection of alendronate-loaded PLGA nanoparticles, and an intravenous injection of alendronate-loaded hydroxyapatite nanoparticle.[11-13]

In orthopedic surgery, the treatment plan for osteoporotic-bone fractures, particularly the biomaterial choice, is widely depended on the fracture site. The current available biomaterials used for osteoporotic-bone repair include metals,[14] polymers,[15] and ceramics. There are a number of drawbacks associated with these biomaterials such as, 1) inadequate mechanical integrity,[8,9] 2) lack of ability to support all irregular shapes of an osteoporotic fracture, and 3) in some cases, these scaffolds are made with non-biodegradable materials and require surgical removal. Therefore, biodegradable and injectable polymeric materials are innovative developments for fracture repair in bone and regenerative medicine. The advantages of degradable materials are 1) they do not require removal post administration; 2) they provide the ability to fine-tune degradation kinetics to degrade in vivo in a controlled manner matching with regeneration time of bone; and 3) they are more capable of penetrating and blending into the fractures leading to better fixation of bones under the minimally invasive surgical technique.

The field of osteoporosis therapies needs new technologies that utilize efficient and cost-effective engineering to create drug/medical devices with 1) high patient adherence and patient compliance, 2) long-acting delivery of anti-osteoporotic drugs, 3) ability to be administered as "injectable" bone-repair biomaterials via intraosseous injection to promote bone healing post-bone fractures and mitigate the need for surgical procedures, or 4) combined with 3D bioprinting technologies, can be engineered as "customized" bone-repair scaffolds with patient-specific fitting (via MRI scan and computer aided design (CAD)) to osteoporotic defect(s) to support and promote bone regeneration. Current developing technologies of injectable long-acting delivery of anti-osteoporotic drugs utilize the generation of nanoparticles, liposomes, or microspheres to manufacture long-acting injectable formulations (LAIs). These technologies are limiting in many ways including a) complex stepwise manufacturing process, b) poor scale-up, c) high cost, d) short shelf life, and e) in some cases toxicity and off target effects. Additionally, current injectable biomaterial technologies being developed to promote bone healing use either aqueous polymer blending with solid cements (i.e. Calcium phosphate), or in-situ curing of synthetic polymers (e.g. polymethylmethacrylate) at the defect sites. These technologies are also limited in many ways including a) complex manufacturing process, b) high costs, c) excessive heating during polymerization of the cement, which can lead to drug degradation, and d) brittleness of the final product. Currently, there are no technologies that combine the use of an in-situ thermoresponsive forming hydrogel (ISTFH) technology with hybridized FDA-approved biopolymers to create bone-repair biomaterials The field of osteoporosis therapies also needs new devices that can 1) provide sustained release of SOC drugs (≥30 days) to replace daily administration and improve patient compliance, 2) enhance efficacy of bone strengthening for treatment of osteoporosis, 3) promote bone healing/regeneration, in event of osteoporotic-bone fracture, and 4) mitigate the need for surgical procedures post-bone fracture to introduce or remove the biomaterial scaffold. The development of biodegradable combinatory devices could be ground breaking, as there are no approved products or products currently in development that can simultaneously address two indications: 1) sustained drug delivery via subcutaneous administration for treatment of osteoporosis, and 2) support bone regeneration post-bone fracture via intraosseous injection/implantation. Developing effective combinatory injectable implants by ISTFH technology will address a critical unmet need by providing a dual effect for treatment of osteoporosis. This task has been challenging due to differences in target drug release rates (for systemic and local delivery), the inability to meet good mechanical properties for intraosseous biomaterial scaffolds, and the inability to support bone regeneration in irregular large osteoporotic defects. Therefore, ISTFH technologies that have the potential to provide precise and tunable control over the drug release rates, mechanical properties, and can be adapted to fit irregular and patient specific shapes are in high demand and represent an unmet need.

As such, provided herein are injectable/3D-bioprinted cellulose nanocrystal-hybridized chitosan based hydrogels fabricated by in-situ thermoresponsive forming hydrogel (ISTFH) technologies for controlled drug release and tissue regeneration support. The instant disclosure utilizes the versatility of ISTFH technologies to engineer new injectable/3D-bioprinted combinatory implants. With ISTFH technologies, injectable combinatory implants are provided that can be applied as: 1) sustained drug delivery, once-a-month or once-every few months treatment, via subcutaneous or intramuscular (IM) administration for bone strengthening; and 2) sustained drug delivery and bone-repair biomaterial scaffold via intraosseous injection/implantation to effectively promote bone regeneration post-bone fracture and mitigate the need for surgical procedures used to introduce current marketed implants such as polymethylmethacrylate (PMMA) cement, and silicone (VK100) cement. These novel injectable/3D-bioprinted combinatory implants are 1) safe, stable, and syringeable solutions at room temperature; 2) bioprintable through commercial extrusion bioprinters; 3) form a gel instantaneously at 37° C.; 4) have good post-gelling mechanical strength (modulus in the rage of 5-380 kPa); 5) can accommodate target drug concentration: 6) supports ≥80% cell viability; and 7) exhibits ability to control cell behaviors to promote bone regeneration. These new combinatory implants can be prepared using FDA-approved thermogelling biopolymers (chitosan, cellulose nanofibers/nanocrystals (CNFs/CNCs)), and SOC drugs (bisphosphonates) for their proved efficacy.[16,17] Chitosan solution can undergo sol-gel transition at body temperature.[18] Its syringeability, ability to form an in-situ implant when injected in the subcutaneous or IM environment or at osteoporotic fracture sites, and ability to form a 3D-bioprinted implant using an extrusion bioprinter make it an ideal candidate as a long-acting injectable/tissue-engineered system and/or scaffold. In the proposed ISTFH formulation, CNFs/CNCs are used as an additive nanomaterial to strengthen the mechanical properties of the chitosan gel and mimic bone tissue properties.[19,20] The combination of CNFs and CNCs to form an in-situ thermogelling implant is unprecedented and will have a versatile impact as a platform technology for long-acting drug delivery and the design of biomaterial implants and scaffolds for bone-repair, regenerative medicine and tissue engineering applications.

In some embodiments, disclosed herein are injectable cellulose nanocrystal-hybridized chitosan based hydrogels fabricated by ISTFH technology that provide superior control over drug release rate compared to other injectable long-acting delivery technologies currently being developed.

In some embodiments, disclosed herein are injectable cellulose nanocrystal-hybridized chitosan based hydrogels fabricated by ISTFH technology that provide better mechanical characteristics to promote bone healing/regeneration compared to other bone-repair biomaterial scaffolds currently being developed.

In some embodiments, the combinatory effect of the injectable cellulose nanocrystal-hybridized chitosan based hydrogels fabricated by ISTFH technology as a subcutaneous/IM and intraosseous delivery modality can improve efficacy for treatment of osteoporosis.

In some embodiments, the disclosed 3D bioprinted cellulose nanocrystal-hybridized chitosan based implants fabricated by ISTFH technology can provide patient "customized" bone-repair scaffold with patient-specific (MRI scan) fitting to osteoporotic defect(s) to support and promote bone regeneration.

In some embodiments, the preparation of injectable cellulose nanocrystal-hybridized chitosan based hydrogels by ISTFH technology described herein are safer and more cost-efficient than using other LAI or biomaterial technologies currently being developed.

In some embodiments, the preparation of implantable cellulose nanocrystal-hybridized chitosan based scaffolds by ISTFH technology described herein are safer and more cost-efficient than using other LAI or biomaterial technologies currently being developed.

In some embodiments, disclosed herein is the fabrication of injectable cellulose nanocrystal-hybridized chitosan based hydrogels using ISTFH technology that can be applied for two indications: 1) long-acting drug delivery for treatment of osteoporosis via a subcutaneous or IM injection, and 2) local drug delivery and bone-repair biomaterial post-bone fracture via an intraosseous injection or implantation, which has not been presented in any current development.

In-situ thermoresponsive forming hydrogel (ISTFH) technology: In situ forming hydrogels are defined as liquid formulations which form a gel in situ after injection into the body via a syringe. In this regard, the in situ forming hydrogels can provide a "customized" drug delivery/medical device, in terms of dose, volume, and filling shape. A polymer solution can be in situ gelled by either photopolymerization, chemical crosslinking, ionic crosslinking, or an environmental stimulus (i.e. temperature, pH or ionic strength of the surrounding medium). Particularly, the in situ forming hydrogels formed by temperature change, are known as in-situ thermoresponsive forming hydrogel (ISTFH), offer several advantages over other in-situ forming systems. These advantages include simple manufacturing process, and absence of organic solvents, initiators, or chemical cross-linkers.

FDA-approved thermogelling chitosan (CS): Among the ISTFH systems, thermogelling chitosan (CS)-based solutions have been extensively investigated. Solutions of thermogelling biocompatible polymers including an amino sugar linked to form a hydrophilic polymer in an acidic environment (e.g., pH below 5.6), such as solutions of thermogelling CS and CS derivatives, such as trimethylchitosan or quaternized chitosan, can undergo sol-gel transition at body temperature upon addition of phosphate molecules (i.e. glycerophosphate, sodium phosphate) and/or polyols.[18] Its intrinsic properties (biocompatibility, biodegradability, bioadhesivity, bacteriostatic effect) and ability to form an in-situ hydrogel when injected into the body make it an ideal candidate as a pharmaceutical and biomedical applications. BST-CarGel® is an innovative product for cartilage repair using thermogelling CS solution to create a liquid bioscaffold, which has been commercially approved and marketed in 2012. However, the CS systems show some potential drawbacks for long-acting drug delivery and bone tissue engineering such as high initial burst release of drug, fast drug release rate, and low mechanical strength to support bone formation. Therefore, incorporation of nanoparticles, microspheres, or liposomes, or secondary polymers into CS-based thermoresponsive hydrogels have been attempted to overcome these limitations.

Cellulose nanofibers/crystals (CNFs/CNCs): Cellulose nanofibers/crystals (CNFs/CNCs) are a unique nanomaterial extracted from natural cellulose fibers. CNFs/CNCs provide very high strength (tensile strength, about 7.5-7.7 GPa) and stiffness properties (elastic modulus, about 110-220 GPa) which make them as an excellent reinforcing agent for many in situ forming hydrogels such as PVA, PEG, hyaluronic acid, and methylcellulose. Prior to this disclosure, there have been no reports on the use of CNCs as an additive nanomaterial into the thermogelling chitosan-based hydrogels for either drug delivery or tissue engineering applications. Described herein is the innovative fabrication of injectable thermoresponsive CNC-hybridized CS based hydrogels for treatment of bone disease and bone-fracture repair. The incorporated CNCs are used for 1) strengthening the mechanical properties of the thermogelling chitosan-based hydrogels to mimic bone tissue environments, 2) promoting gelling time to minimize drug burst release and maximize drug entrapment efficiency, and 3) control degradation rate of thermogelling chitosan-based hydrogels to promote sustained drug release over 30 days or longer.

3D bioprinting technology: Bioprinting has potential for regenerating large, irregular-shaped osteoporotic defects; however, there is a limited number of printable biomaterials that can provide the required physical/mechanical properties to support these osteoporotic defects. Engineering new bioinks is challenging since the material properties for extrusion-based bioprinting are not yet well-known. There is a significant need for the novel bioinks for 3D bioprinting to create a biomaterial supporting bone regeneration. Therefore, disclosed herein is the development of a CNC-hybridized CS based bioink with rheological properties suitable for bioprinting to advance a new bioink development.

In addition to osteoporosis, the compositions and formulations of the present disclosure can be applicable for use in treating and/or preventing various disorders beyond osteoporosis. For example, such disorders can include, but are not limited to: Paget's disease; cancer; diabetes; and infectious diseases. Furthermore, the compositions and formulations of the present disclosure can have applications in treating or preventing disorders through regenerative medicine, including bone regeneration and/or tissue regeneration.

EXAMPLES

The present disclosure will now be described with reference to the following examples. It should be appreciated that these examples are not intended to limit the scope of the claims to the present disclosure, but are rather intended to be exemplary of certain embodiments. The instant disclosure includes numerous alternatives, modifications, and equivalents as will become apparent from consideration of the following example and claims. Any variations in the exemplified methods that occur to the skilled artisan are intended to fall within the scope of the present disclosure.

Example 1

Materials and Methods

Extraction of Cellulose Nanocrystals (CNCs) Using Acid Hydrolysis

CNCs were prepared by acid hydrolysis using sulfuric acid under ultrasonication using a sonication bath. Briefly, 10 g of cotton cellulose (WHATMAN® ashless filter-aid paper) was added in 50% (v/v) of aqueous sulfuric acid. The suspension was held at 45° C. under sonication for 10 min. The suspension was subsequently diluted with cold deionized water to stop the hydrolysis, followed by centrifugation at 6,000 rpm for 10 min. The solid aggregates in the suspension were collected and disrupted by sonication for 1 h. The suspension was then centrifuged at 6,000 rpm for 10 min to remove traces of sulfate salts and washed with deionized water. The collected suspension was dialyzed using a dialysis membrane (SNAKESKIN® dialysis tubing, MWCO 7,000 Da) against deionized water until neutrality of the dialysis effluent. The resulting CNC suspension was freeze-dried in a lyophilizer (VirTis SP Scientific, Benchtop K Lyophilizer) under (−60° C., 0.1 mbar) and stored at 4° C.

TEM Analysis of CNCs

The morphology of extracted CNCs was characterized using Transmission Electron Microscopy (TEM, JEOL JEM 1230). The 0.1% (w/v) of CNC suspension was dropped onto copper grids coated with a carbon support film.

Zeta Potential Measurement of CNCs

Electrophoretic mobilities of the isolated CNCs were measured on a Zetasizer Nano ZS (Malvern Instrument, Malvern, United Kingdom). The 0.1% (w/v) of samples prepared in 0.1 M sodium chloride were placed in a dip-coated zeta cell at a temperature of 25° C. Mobility values were converted to z-potentials using the Smoluchowski equation and reported values are an average of 30 measurements.

Formation of Injectable Cellulose Nanocrystal-Hybridized Chitosan (CS-CNC) Based Hydrogels A 3% (w/w) chitosan solution was prepared by stirring chitosan powder in 1% (v/v) aqueous acetic acid at room temperature overnight. The β-glycerophosphate (GP), glycerol, and CNCs were used as their powder forms. In order to form the in-situ thermogelling hydrogels, all compositions were first separated into two systems: the first system consisted of a 3% chitosan solution, and the second system consisted of a mixture of gelling agents, CNCs, and deionized water. The second system was transferred into the chitosan system to create the pre-hydrogel mixture, followed by incubation at 37° C. for 5 min to create a hydrogel. Details of the screened formulations for optimization are represented in Table 1 (concentrations of each composition represent the final concentration after mixing).

TABLE 1

The screened formulations of injectable CS-CNC hydrogels

| Polymers | | CNCs | | Gelling agent | |
|---|---|---|---|---|---|
| Type | Conc. (% w/w) | Type | Conc. (% w/w) | Type | Conc. (% w/w) |
| Chitosan (250 kDa) | 1-3% | Negatively charged CNC | 0-2% | β-GP Glycerol Mannitol | 1-20% 3-10% 3-10% |

Measurement of Gelation Time

The gelation time of the hydrogels was determined by RSAIII micro-strain analyzer (TA Instruments, United States of America) fitted with a parallel plate geometry and a circulating environmental system for temperature control. The dynamic time sweep testing was used to study the sol-gel transition behavior of the hydrogel formulations. A fresh solution or suspension was poured into the parallel plate instrument and the experiment was then conducted at 37° C., an angular frequency ($\omega$) of 1 rad/s, and a strain amplitude of 10%. The gelation time was determined as a time of crossover of storage (E') and loss modulus (E").

Dynamic Rheological Measurements

Dynamic rheology measurements were performed on RSAIII micro-strain analyzer (TA Instruments, United States of America) fitted with a parallel plate geometry and a circulating environmental system for temperature control. The strain amplitude was set as 10% for all the measurements, which was within a linear viscoelastic region. For each measurement, a fresh solution or suspension was poured into the parallel plate instrument and had been kept at 37° C. until gelling with additional time for 2 min. Dynamic frequency sweep testing (0.1-100 rad/s) at 37° C. was performed to compare the modulus of the formed hydrogels.

pH and Osmolarity Measurements pH and osmolarity of the pre-hydrogel formulations were determined using pH meter Orion Star A111 (Thermo Scientific), and model 3320 micro-osmometer (Advanced Instruments, Inc.).

Swelling Properties

The swelling properties of the hydrogels, including degree of swelling and gel fraction, were determined. For the degree of swelling test, the weight of the sample was determined before ($W_{initial}$) and after incubation in PBS at 37° C. for different time points ($W_{time}$). At each time point, the degree of swelling or degree of shrinkage was expressed as follows:

Degree of swelling (%)=($W_{time}-W_{initial}$))/$W_{initial}$×100

Degree of shrinkage (%)=($W_{initial}-W_{time}$)/$W_{initial}$×100

When the $W_{time}$ reached a stability (no change between two consecutive measurements), the samples were dried using a freeze-drying process for 24 h (SP VirTis Advantage XL-70, Warminster, Pennsylvania, United States of America) and the dry weight was determined ($W_{dry}$). The percentage gel fraction, representing the portion of the sample that is reacted into the crosslinked network, was expressed as follows:

Gel fraction (%)=($W_{dry}/W_{initial}$)×100

Microstructure Analysis by Scanning Electron Microscopy (SEM) Imaging

Microstructures of the hydrogels were evaluated by scanning electron microscopy (SEM). To investigate the effect of CNCs on the microstructure of the hydrogels, samples prepared by the protocol mentioned above and incubated in PBS (10 mL, pH 7.4, 37° C.) for 24 h, and 42 days. The samples were removed from PBS, flash frozen with liquid nitrogen, and then lyophilized for 24 h (SP VirTis Advantage XL-70, Warminster, Pennsylvania, United States of America). The lyophilized samples were subsequently fractured and mounted on an aluminum stub using carbon tape, and sputter coated with 5 nm of gold-palladium alloy (60:40) (Hummer X Sputter Coater, Anatech, Union City, California, United States of America). The coated samples were imaged using a Zeiss Supra 25 field emission scanning electron microscope with an acceleration voltage of 5 kV, 30 μm aperture, and average working distance of 11 mm (Carl Zeiss Microscopy, LLC, Thornwood, New York, United States of America).

High Performance Liquid Chromatography (HPLC) Analysis of Release BGP

To confirm the gelation process of CS system with BGP, the amount of released BGP was quantified after the hydrogel weight maintained stability at 42 days. Sample aliquots (1 mL, n=3) were collected from the incubation medium (PBS, pH 7.4). BGP concentration in the aliquots was determined by HPLC analysis. A reverse-phase HPLC analysis was carried out with a Finnigan Surveyor HPLC system (Thermo Finnigan, San Jose, California, United States of America) with a Photodiode Array (PDA) Plus Detector, auto-sampler, and LC Pump Plus. The stationary phase utilized for the analysis was an Inertsil ODS-3 column (4 μm, 4.6 Å~150 mm, GL Sciences, Torrance, California, United States of America) maintained at 40° C. Chromatographic separation was achieved by gradient elution using a mobile phase consisting of water and ACN ($H_2O$/ACN 10:90 v/v). The flow rate was 0.4 mL/min and the total run time was 13 min for each 25 μL injection.

Fourier Transform Infrared Spectroscopy (FTIR) Analysis of the Interaction of Hydrogel Network Fourier Transform Infrared Spectroscopy (FTIR) was used to characterize the presence of specific chemical groups in the hydrogel materials. CS and CS-CNC hydrogels in gel states (in water, and in deuterated water) and dry state were obtained with 1 mm thickness and analyzed by Attenuated Total Reflection (ATR)-FTIR using Absorbance Mode. FTIR spectra were obtained in the range of wavenumber from 4000 to 600 $cm^{-1}$ using 64 scans, with 4 $cm^{-1}$ resolution (Tensor II, OPTIK Instruments).

Cell Culture

The MC3T3-E1 subclone 4 (ATCC CRL-2593) is a preosteoblast cell line isolated from mouse calvaria and is a model to study cytotoxicity and cell behaviors inside the hydrogels as potential use for bone tissue engineering and cell therapy. Cell lines were grown in complete growth media, containing dulbecco's modified eagle media (DMEM) (Corning) with 10% fetal bovine serum (FBS) (Atlanta Pharmaceuticals) under 5% $CO_2$ at 37° C.

Viability and Proliferation of Encapsulated Cells in the Hydrogels

The hydrogel solutions (3 syringes) at final 1 mL were first prepared under sterile conditions. Then, the MC3T3-E1 were trypsinized and mixed into the hydrogel solutions at a density of 1 million cells/mL of hydrogel and cultured in 8-well chamber slide (Nunc™ Lab-Tek™ Chamber Slide) with complete growth media. Media was changed every two days. After 24 h and 7 days of cell culture, the media were removed, and the hydrogels were washed with PBS thrice. The prepared Live/Dead assay reagent, 1 μM Calcein AM and 2 μM Ethidium Homodimer-1 (EthD, Molecular Probes, Inc., USA) was added to the hydrogels and incubated for 45 min at 37° C. The samples were washed with PBS thrice, and imaged using a laser scanning confocal microscope (Zeiss LSM700), collection of 12 Z-stacks from each sample with 5× lenses.

Morphology of Encapsulated Cells in the Hydrogels

After 24 and 72 h culture, the cell-encapsulated hydrogels were fixed in cold 4% paraformaldehyde for 20 min and washed in PBS thrice, followed by incubation in a 0.2% tween20 for 10 min. The samples were then stained with 0.165 μM Acti-stain phalloidin and 100 nM 4',6-diamidino- 2-phenylindole (DAPI) solution at 37° C. for 30 min according to manufacturer's protocol. The samples were imaged using a laser scanning confocal microscope (Zeiss LSM700), collection of 12 2D images from each sample with 10× lenses.

Optimization of CS-CNC Formulations as a Bioink for 3D Bioprinting

In order to form in-situ CS-CNC bioinks, all compositions were first separated into two systems: the first system consisted of a 3% chitosan solution, and the second system consisted of a mixture of gelling agents, CNCs, and deionized water. The second system was transferred into the chitosan system to create the pre-hydrogel mixture, followed by centrifugation at 4000 rpm, 25° C. for 5 min to remove all air bubbles in the formulation. Details of the screened formulations for optimization are represented in Table 2 (concentrations of each composition represent the final concentration after mixing).

TABLE 2

The screened formulations of CS-CNC bioinks

| CS (% w/v) | Gelling agent | | CNC (% w/v) |
|---|---|---|---|
| | BGP (mM) | HEC (mg/mL) | |
| 2 | 100 | 0.1-0.5 | 0-2 |

Rheological Property Assessment for Bioinks

Anton-Paar's Modular Compact Rheometer 302 (MCR) was selected to evaluate viscosity, yield stress and storage modulus recovery. All tests were conducted at 25° C. and with a gap of 100 µm. The 3% chitosan solution was used to optimize all testing protocols (n=3). Viscosity curves were determined by a logarithmic shear rate sweep from a shear rate of 0.1 $s^{-1}$-100 $s^{-1}$ with 5 points per decade. The yield stress was determined by an oscillatory shear strain sweep from 0.1% to 200% at frequency of 1 Hz with 5 points per decade, and the yield stress was defined as the shear stress at the crossover point of the storage (G') and loss (G") moduli. Finally, the storage modulus recovery was determined by three phases of oscillatory shearing at a frequency of 1 Hz after a 5-min soak time where no stresses were applied. Then the materials underwent the following:

1. 2 min of a constant shear strain of 1% to determine an initial storage modulus;
2. 30 s of high shear strain of 60% (above the material's yield stress to mimic extrusion and flow through a bioprinter nozzle); and
3. 2 min of a constant shear strain of 1%.

The initial storage modulus was defined by the average storage modulus of the initial 2 min of the material being exposed to 1% of shear strain. The recovered storage modulus was defined by the storage modulus 10 s after the shear strain transitioned from 60% back to 1%. The percent recovery was defined as:

$$\frac{\text{Recovered storage modulus}}{\text{Initial storage modulus}} \times 100$$

Example 2

Prototype Cellulose Nanocrystals (CNCs) Fabricated Using Acid Hydrolysis

CNC can be isolated from different natural cellulose sources via different hydrolysis conditions. Herein, CNC was successfully extracted from cotton cellulose using sulfuric acid hydrolysis assisted with ultrasonic treatment at optimum conditions (Table 3). The nanocrystalline fragments of cellulose were produced due to the action of acid breaking down the glucosidic linkages of the amorphous region of cellulose. The ultrasonication and temperature (used at 45° C.) promote the hydrolytic action of acid in a short time with high yield. Type of acid had a significant impact on the stability of synthesized CNCs. Sulfuric acid was found to be the best suitable acid to generate stable and re-dispersible CNCs due to the electrostatic repulsion of negatively charged sulfate groups reacted to hydroxyl groups of CNCs. This was also confirmed by the surface charge analysis and zeta potential data illustrated in Table 3.

The morphology of the isolated CNCs was investigated under a transmission microscope at randomized areas, and sizes of the CNCs were identified based on the images. FIG. 1 confirmed that sulfuric acid successfully extracted CNCs from cotton celluloses into nanoscale rod-like structures. The calculated length and diameter of the nanorods synthesized by different acid concentration and duration were similar in range, and ranged from 100-200 nm and 10-20 nm, respectively. Using 50% (v/v) of sulfuric acid assisted with ultrasonic treatment at 45° C. for 10 min was found to be a suitable and reproducible method for the synthesis of CNCs with optimum time and efficiency.

TABLE 3

Various conditions used for isolation of CNCs and their results

| Acid type | Conc. (% v/v) | Time | CNC yield | Zeta potential (mV) |
|---|---|---|---|---|
| $H_2SO_4$ | 60% | 1 min | Unyielded CNCs | N/A |
| | 50% | 10 min | High yielded CNCs | −14.7 ± 0.11 |
| | 40% | 60 min | Medium yielded CNCs | −15.6 ± 1.31 |

Example 3

Prototype Injectable CS-CNC Hydrogels Fabricated Using In-Situ Thermogelling Process The injectable CNC-CS hydrogels were accomplished using in-situ thermogelling process. Unlike other thermogelling chitosan-based hydrogel technologies, the in-situ thermogelling process of this ISTFH system is promoted by combination of the hydroxyl groups and negative charges of CNCs and the use of traditional gelling agents such as β-GP, glycerol and mannitol. This combination is unprecedented and pertains to the innovation of the proposed ISTFH system.

In order to generate a set of prototype injectable CNC-CS hydrogels, formulation parameters related to compositions ratios were first screened and optimized through the following criteria: 1) low viscosity (<800 cP), 2) syringeability through 25 G needles at room temperature, and 3) optimum pH (6.5-7.5) and osmolarity (260-400 mOsm/kg) to support cell viability for bone regeneration application. Three injectable CNC-CS hydrogels using different concentration of CNCs (0, 0.5, 1, 2% w/w) were selected as prototypes and fabricated by the in-situ thermogelling process as shown in Table 4. Due to their intrinsic hydrophilic properties, SOC drugs of osteoporosis such as alendronates are easily loaded in the injectable CNC-CS hydrogels (up to 20 mg/mL which is far beyond the drug-loading target at >5 mg/mL). These prototypes were consequently evaluated and optimized to meet the following criteria: 1) instantaneous gelling at 37° C. for efficient drug entrapment in vivo; 2) good post-gelling mechanical strength (compression force=10-20 kPa); 3) can accommodate target drug concentration; 4) supports >80% cell viability; and 5) exhibits ability to control cell behaviors to promote bone regeneration for bone fractures.

TABLE 4

The prototype injectable CS-CNC formulations with their pH and osmolality (n = 3).

| Hydrogel | Gelling agent | | | | pH | Osmolality (mOsmol/kg) |
| --- | --- | --- | --- | --- | --- | --- |
| | CS (% w/v) | BGP (mM) | HEC (mg/mL) | CNC (% w/v) | | |
| CS | 2 | 100 | 0.5 | 0 | 6.64 | 357 ± 15 |
| CS + 0.5% CNC | 2 | 100 | 0.5 | 0.5 | 6.68 | 373 ± 6 |
| CS + 1.0% CNC | 2 | 100 | 0.5 | 1.0 | 6.69 | 373 ± 12 |
| CS + 2.0% CNC | 2 | 100 | 0.5 | 2.0 | 6.71 | 390 ± 9 |

Example 4

The Effect of CNCs on the Physical and Mechanical Properties of the CS Hydrogels.

Gelation Time

Based on the rheological measurement as shown in FIG. 2A, the gelation time of all prototype hydrogels was less than a minute. Specifically, the gelation time of the CNC-CS hydrogels (less than 7 s, n=3) was more instantaneous and consistent than the injectable CS hydrogels (approximately 24±17 s, n=3). The synergistic effect of CNCs on gelation kinetics of the CS hydrogels is likely due to the interaction of CNCs and CS through hydrogen bonding. The instantaneous gelling at 37° C. of the injectable CNC-CS hydrogels is an ideal property for not only tissue engineering but also drug delivery since it promotes drug entrapment efficiency, inhibits high burst drug release, promotes controlled and sustained drug, release and avoids any leakage of the materials to non-target surrounding tissues.

Mechanical Testing

The mechanical test results demonstrate that CNCs can reinforce stiffness and toughness of the thermogelling CS hydrogel (FIG. 2B). The elastic modulus of CNC-CS hydrogels was approximately 379 kPa when using 2% w/w of CNCs (n=3), 111 kPa when using 1% w/w of CNCs (n=3), 86 kPA when using 0.5% w/w of CNCs (n=3) compared to 28 kPa (n=3) in CS hydrogels without CNCs. These excellent mechanical properties of the thermogelling CNC-CS hydrogels will promote a number of benefits for bone-fracture repair applications such as but not limited to osteogenesis and bone tissue formation. In addition, these hydrogels can easily integrate and blend with surrounding bone tissue environment and promote efficient bone support and repair.

Swelling Behaviors and Gel Fraction

The degree of swelling reveals that CS and CS-CNC hydrogels rapidly decreased in the first week and slowly continued to decrease overtime. Up to 28 days post incubation in PBS, the hydrogels maintained their weight (FIG. 3A, C). Without being bound by any particular theory or mechanism of action, this phenomenon can be explained by the hydrophobic interaction of CS and the disruption of ionic interaction of CS and BGP in PBS (pH 7.4), leading to rapid shrinkage of the hydrogels during first 24 h. The further shrinkage of hydrogels overtime after 24 h can be the result of continuous diffusion of unreacted BGP in CS/BGP system into PBS. In addition, the gel fraction results provide a clear evidence of the diffusion of BGP from the CS networks. More importantly, this data showed that the introduced CNC was completely reacted into CS networks from the matching percentage of gel fraction to the amount of CNC introduced into the system. This result demonstrates that CNCs can significantly increase the crosslink density of the CS/GP hydrogels and impede the degree of shrinkage in CS/GP system (FIG. 3B).

Microstructure

The SEM micrographs of the hydrogels clearly support the shrinkage properties and mechanical properties of CS and CS-CNC hydrogels. Specifically, the microstructure of all hydrogels after gelling provided a wide range of pore sizes from 20-500 µm. The thicker interconnecting walls and denser porosities were observed in the CS systems with higher amount of CNCs incorporated, resulting in enhanced mechanical properties of the hydrogels. Once the hydrogels were immersed into PBS pH 7.4, the hydrophobic interaction of CS was promoted and ionic interaction of CS and BGP was eliminated leading to shrinkage of the hydrogels. However, presence of CNCs in the hydrogel matrix can partially impede hydrophobic interactions of CS through hydrogen bonding and results in networks with higher crosslink density. This was shown in the SEM images of the hydrogels after 1 day, and 42 days in PBS (FIG. 3D). As result, the CS-CNC hydrogels showed lower degree of shrinkage compared to the CS hydrogels.

Example 5

The Interaction of CNCs in CS Hydrogels

The role of CNCs in reinforcing the hydrogel networks can be attributed to the non-covalent interaction of surface functionalized CNC to CS backbone, and the possible interaction of CNCs in the CS/GP system is shown in FIG. 4A-B. At pH 7.4 in PBS and 37° C., most charged amine functional groups on CS backbone that were initially solvated by BGP became deprotonated and uncharged, leading to the hydrophobic interaction between CS chains. However, the sole hydrophobic interaction of CS was not sufficient to create a strong hydrogel network. The reactive glyoxal molecules from HEC are required to crosslink with the amine groups of CS and result in a hydrogel. By further introducing CNCs, CS chains can interact to CNCs through mostly hydrogen bonding. Herein, FTIR was used to probe the role of CNC reinforcement of the CS network. When comparing the IR spectra of gels in their gel state to those of gels in their solid state compositions (CS and CNC), a broadening and shift of vibrational band was observed at 3250-3300 to 3400 cm$^{-1}$, which attributes to the characteristic of hydrogen bonding[21] of CNCs and CS (FIG. 4C). The replacement of water with deuterated water was necessary in order to rule out the hydrogen bonding from water.[22,23] The FTIR spectra showed that the intensity at 3400 cm$^{-1}$ was related to the concentration of incorporated CNCs (shown in FIG. 4D). The C═N stretching at the absorbance of 2360 cm$^{-1}$ was also observed in the FTIR spectra of the CS and CS-CNC hydrogels in gel states in the presence of water, confirming the presence of chemical crosslinking of glyoxal molecules from HEC and the amine group of CS.

TABLE 5

FTIR assignment of different chitosan hydrogel formulations immersed in deuterium dioxide (D$_2$O) (in FIG. 4C).

| Wavenumber (cm$^{-1}$) | Assignments |
|---|---|
| 3400 (strong and broad) | —OH and —NH stretching, intermolecular hydrogen-bonding |
| 2915 | C—H stretching |
| 2855 | C—H stretching |
| 2470 (strong) | O—D stretching (D$_2$O) |
| 1650 | N—H bending, |
| 1460 | C—H bending, |
| 1200 | O—-D bending (D$_2$O) |

Example 6

The Effect of CS-CNC Hydrogels on Cellular Behaviors.

The biocompatibility of the CS-CNC hydrogels and their potential use as a tissue engineered scaffold were determined by LIVE-DEAD staining of encapsulated pre-osteoblast cells (MC3T3-E1). The MC3T3-E1 cells were selected as the cell model owing to potential application for bone tissue engineering. The materials were compatible to support mostly 100% cell viability for at least 7 days, although there was no significant cell proliferation observed in all hydrogel groups (FIG. 5), which is due to the hydrophobicity of CS leading to decreased cell adhesion. The cell morphology of the encapsulated cells was further observed in CS hydrogels compared to CS-CNC hydrogels using Acti-stain phalloidin and DAPI staining cytoskeleton and nucleus, respectively. It was found that the morphology of encapsulated cells in CS-CNC networks was more spreading with a strong cytoskeleton structure after 3-day culture. While the encapsulated cells in CS networks were mostly in circular morphology after 3-day culture. It is well-accepted that cellular behavior of encapsulated cells is controlled by their microenvironment cues including mechanical stiffness, biochemical factors, and ligands.[24-26] The mechanical stiffness of their networks plays a critical role in governing cell shape which profoundly impacts cell fate via intracellular signaling.[27] Specifically, soft extracellular matrix less than 5 kPa support spherical morphology of encapsulated cells and facilitate adipogenesis. In contrast, stiff microenvironment support cell spreading, strong cytoskeleton, and promote osteogenesis of the encapsulated cells. Therefore, the disclosed nanoengineered CNC-CS hydrogel can be used to engineer cell-matrix interaction via modulating the mechanical properties of the hydrogel systems.

The instant disclosure demonstrates that the use of these hydrogels can be expanded beyond osteoporosis by encapsulating induced neural stem cells (iNSCs) for treatment of Glioblastoma multiforme (GBM). In these studies, mouse neural stem cells (1×10$^6$ cells/scaffold), C17.2, were encapsulated in 1 mL of hydrogel and seeded directly into an 8 well chamber glass slide (Nunc Lab-Tek Chamber Slide System™) to investigate stem cell persistence. Results showed that the encapsulated iNSCs were viable in both CS and CS-CNC hydrogels for at least 9 days without proliferation similar to the results observed in MC3T3-E1 cells. This data shows the broad range of applications of these hydrogels for multiple indications (e.g. osteoporosis, cancer treatment, tissue engineering and other) and multiple uses within one indication (i.e. s.c. injectable, intraosseous injectable, bioink and implant for osteoporosis).

Example 7

Optimized CS-CNC Bioink Formulations for 3D Bioprinting

The injectable CS-CNC formulations were further optimized and utilized as bioinks for 3D bioprinting. The CS-CNC hydrogel precursors exhibit shear-thinning fluid properties which are one of the desirable characteristics for bioinks. Bioink prototypes (Table 6) that meet the following criteria were screened and selected: 1) printability using commercial 3D bioprinters, 2) consistent flow properties for ease of extrusion, and 3) fast gelation post printing to maintain bioprint shape/size integrity (compared to CAD dimensions generated from patient MRI scan). The optimization process of 3D bioprinting is shown in FIG. 6. Briefly, bioinks containing CS, BGP, HEC, CNCs and cells were mixed and loaded into 3D-bioprinter cartridges. The CS-CNC bioinks were bioprinted using a CAD structure onto a cell-culture glass coverslip under sterile conditions. The bioprinted CS-CNC bioinks were subsequently crosslinked by temperature stimulation at 37° C. for 15 min. Tissue-culture medium was added to culture the scaffolds.

TABLE 6

The detail of optimized bioink formulations

| | | Gelling agent | | |
|---|---|---|---|---|
| Hydrogel | CS (% w/v) | BGP (mM) | HEC (mg/mL) | CNC (% w/v) |
| CS | 2 | 100 | 0.1 | 0 |
| CS + 0.5% CNC | 2 | 100 | 0.1 | 0.5 |
| CS + 1.0% CNC | 2 | 100 | 0.1 | 1.0 |
| CS + 1.5% CNC | 2 | 100 | 0.1 | 1.5 |

Example 8

The Rheological Properties of Prototype CS-CNC Bioinks
Viscosity (Shear-Thinning Properties)

Viscosity is an important parameter to characterize a bioink formulation because it determines how much pressure is necessary to extrude a material at a desired flow rate. In general, materials with high viscosity can maintain their shape after printing better than low viscosity materials. However, a material needs to be able to flow through a needle, and therefore viscous bioinks are required to have shear thinning behavior. The data here show that all optimized bioinks (with or without CNC incorporated) exhibited shear-thinning behaviors (FIG. 7A). The average initial viscosities of the CS, CS-0.5% CNC, CS-1% CNC, CS-1.5% CNC bioinks were 250, 320, 240, and 410 Pa·s, respectively (FIG. 7B).

Yield Stress

The yield stress is also an important parameter to characterize since a yield stress can be useful for a material to hold its shape after bioprinting and support the weight of added layers during the bioprinting process. The average yield stress of the CS, CS-0.5% CNC, CS-1% CNC, CS-1.5% CNC bioinks was 410, 400, 445, and 535 Pa, respectively (FIG. 7C). It was also observed that all CS-CNC bioinks with a yield stress below a value of ~600 Pa can be printable, while with a higher yield stress (i.e. 2% CS-2% CNC bioink) resulted in bioprints with fractured and irregular lines. It should be noted that the yield stress limits are different for different size nozzles or bioink materials and therefore can be adapted as needed.

Storage Modulus Recovery

The storage modulus recovery is an important parameter to determine how well original properties are recovered after printing. The results showed that all bioink formulations provided recovery more than 90% from their initial storage modulus properties (FIG. 7D), which further confirmed the ability to use these formulations with a 3D bioprinter and high printing fidelity.

Example 9

Printability of Prototype 3D Bioprinted CS-CNC Scaffolds

Various printing path designs including straight-line, cross-line, and honeycomb designs were performed in the control CS bioinks. It was found that bioinks were smoothly extrudable through a 22 G nozzle tip with the precise structure close to the original designs (CAD) (FIG. 8A-C). Moreover, the results showed that the bioinks can be precisely printed in a 3D solid structure of knee meniscus model from a patient (MRI scan) without collapsing. Collectively, this data demonstrates the broad and promising utility of the responsive CNC-CS hydrogels as an injectable and/or a bioink for cell therapy and tissue engineering.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

(1) Cosman, F.; de Beur, S. J.; LeBoff, M. S.; Lewiecki, E. M.; Tanner, B.; Randall, S.; Lindsay, R. Clinician's Guide to Prevention and Treatment of Osteoporosis. *Osteoporos. Int.* 2014, 25, 2359-2381.

(2) In *Bone Health and Osteoporosis: A Report of the Surgeon General*, Rockville (MD), 2004.

(3) Temmerman, A.; Rasmusson, L.; Kubler, A.; Thor, A.; Quirynen, M. An Open, Prospective, Non-Randomized, Controlled, Multicentre Study to Evaluate the Clinical Outcome of Implant Treatment in Women over 60 years of Age with Osteoporosis/Osteopenia: 1-Year Results. *Clin. Oral Implants Res.* 2017, 28, 95-102.

(4) International Osteoporosis Foundation Key Statistics for North America. https://www.iofbonehealth.org/facts-statistics#category-23 (9 January), (5) Cramer, J. A.; Gold, D. T.; Silverman, S. L.; Lewiecki, E. M. A Systematic Review of Persistence and Compliance with Bisphosphonates for Osteoporosis. *Osteoporos. Int.* 2007, 18, 1023-1031.

(6) Black, D. M.; Delmas, P. D.; Eastell, R.; Reid, I. R.; Boonen, S.; Cauley, J. A.; Cosman, F.; Lakatos, P.; Leung, P. C.; Man, Z.; Mautalen, C.; Mesenbrink, P.; Hu, H.; Caminis, J.; Tong, K.; Rosario-Jansen, T.; Krasnow, J.; Hue, T. F.; Sellmeyer, D.; Eriksen, E. F.; Cummings, S. R. Once-Yearly Zoledronic Acid for Treatment of Postmenopausal Osteoporosis. *N. Engl. J. Med.* 2007, 356, 1809-1822.

(7) Kwong, F. N. K.; Harris, M. B. Recent Developments in the Biology of Fracture Repair. *JAAOS—Journal of the American Academy of Orthopaedic Surgeons* 2008, 16, 619-625.

(8) Mikael, P. E.; Nukavarapu, S. P. Functionalized Carbon Nanotube Composite Scaffolds for Bone Tissue Engineering: Prospects and Progress. *Journal of Biomaterials and Tissue Engineering* 2011, 1, 76-85.

(9) Burg, K. J.; Porter, S.; Kellam, J. F. Biomaterial Developments for Bone Tissue Engineering. *Biomaterials* 2000, 21, 2347-2359.

(10) Kennel, K. A.; Drake, M. T. Adverse Effects of Bisphosphonates: Implications for Osteoporosis Management. *Mayo Clin. Proc.* 2009, 84, 632-638.

(11) Orellana, B. R.; Hilt, J. Z.; Puleo, D. A. Drug Release from Calcium Sulfate-Based Composites. *Journal of biomedical materials research. Part B, Applied biomaterials* 2015, 103, 135-142.

(12) Bae, J.; Park, J. W. Preparation of an Injectable Depot System for Long-Term Delivery of Alendronate and Evaluation of Its Anti-Osteoporotic Effect in an Ovariectomized Rat Model. *Int. J. Pharm.* 2015, 480, 37-47.

(13) Ezzati Nazhad Dolatabadi, J.; Hamishehkar, H.; Valizadeh, H. Development of Dry Powder Inhaler Formulation Loaded with Alendronate Solid Lipid Nanoparticles: Solid-State Characterization and Aerosol Dispersion Performance. *Drug Dev. Ind. Pharm.* 2015, 41, 1431-1437.

(14) Andani, M. T.; Shayesteh Moghaddam, N.; Haberland, C.; Dean, D.; Miller, M. J.; Elahinia, M. Metals for Bone Implants. Part 1. Powder Metallurgy and Implant Rendering. *Acta Biomater* 2014, 10, 4058-4070.

(15) Golz, T.; Graham, C. R.; Busch, L. C.; Wulf, J.; Winder, R. J. Temperature Elevation During Simulated Polymethylmethacrylate (Pmma) Cranioplasty in a Cadaver Model. *Journal of clinical neuroscience: official journal of the Neurosurgical Society of Australasia* 2010, 17, 617-622.

(16) American Academy of Family Physicians Diagnosis and Management of Osteoporosis. https://www.aafp.org/afp/2015/0815/p261.html (9 January),

(17) National Guideline, C. Diagnosis and Treatment of Osteoporosis. https://www.guideline.gov/summaries/summary/47543/diagnosis-and-treatment-of-osteoporosis

(18) Supper, S.; Anton, N.; Seidel, N.; Riemenschnitter, M.; Curdy, C.; Vandamme, T. Thermosensitive Chitosan/Glycerophosphate-Based Hydrogel and Its Derivatives in Pharmaceutical and Biomedical Applications. *Expert Opin Drug Deliv* 2014, 11, 249-267.

(19) De France, K. J.; Chan, K. J.; Cranston, E. D.; Hoare, T. Enhanced Mechanical Properties in Cellulose Nanocrystal-Poly(Oligoethylene Glycol Methacrylate) Injectable Nanocomposite Hydrogels through Control of Physical and Chemical Cross-Linking. *Biomacromolecules* 2016, 17, 649-660.

(20) You, J.; Cao, J.; Zhao, Y.; Zhang, L.; Zhou, J.; Chen, Y. Improved Mechanical Properties and Sustained Release Behavior of Cationic Cellulose Nanocrystals Reinforeced Cationic Cellulose Injectable Hydrogels. *Biomacromolecules* 2016, 17, 2839-2848.

(21) Sudheesh Kumar, P.; Lakshmanan, V.-K.; Anilkumar, T.; Ramya, C.; Reshmi, P.; Unnikrishnan, A.; Nair, S. V.; Jayakumar, R. Flexible and Microporous Chitosan Hydrogel/Nano Zno Composite Bandages for Wound Dressing: In Vitro and in Vivo Evaluation. *ACS applied materials & interfaces* 2012, 4, 2618-2629.

(22) Suzuki, M.; Yumoto, M.; Shirai, H.; Hanabusa, K. Supramolecular Gels Formed by Amphiphilic Low-Molecular-Weight Gelators of Nα, Nε-Diacyl-L-Lysine Derivatives. *Chemistry—A European Journal* 2008, 14, 2133-2144.
(23) Miljanić, S.; Frkanec, L.; Biljan, T.; Meić, Z.; inić, M. Surface-Enhanced Raman Scattering on Colloid Gels Originated from Low Molecular Weight Gelator. *Journal of Raman Spectroscopy: An International Journal for Original Work in all Aspects of Raman Spectroscopy, Including Higher Order Processes, and also Brillouin and Rayleigh Scattering* 2008, 39, 1799-1804.
(24) Cha, C.; Shin, S. R.; Gao, X., Annabi, N.; Dokmeci, M. R.; Tang, X. S.; Khademhosseini, A. Controlling Mechanical Properties of Cell-Laden Hydrogels by Covalent Incorporation of Graphene Oxide. *Small (Weinheim an der Bergstrasse, Germany)* 2014, 10, 514-523.
(25) Maturavongsadit, P.; Bi, X.; Metavarayuth, K.; Luckanagul, J. A.; Wang, Q. Influence of Cross-Linkers on the in Vitro Chondrogenesis of Mesenchymal Stem Cells in Hyaluronic Acid Hydrogels. *ACS applied materials & interfaces* 2016.
(26) Maturavongsadit, P.; Luckanagul, J. A.; Metavarayuth, K.; Zhao, X.; Chen, L.; Lin, Y.; Wang, Q. Promotion of in Vitro Chondrogenesis of Mesenchymal Stem Cells Using in Situ Hyaluronic Hydrogel Functionalized with Rod-Like Viral Nanoparticles. *Biomacromolecules* 2016, 17, 1930-1938.
(27) Murphy, W. L.; McDevitt, T. C.; Engler, A. J. Materials as Stem Cell Regulators. *Nature materials* 2014, 13, 547.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A pharmaceutical composition comprising:
   a pharmaceutically active agent, wherein the pharmaceutically active agent comprises a bisphosphonate or a teriparatide, or a pharmaceutically acceptable salt of a bisphosphonate or a teriparatide;
   a cellulose nanocrystal or a cellulose nanofiber;
   a thermogelling biocompatible polymer, wherein the thermogelling biocompatible polymer is a chitosan or a chitosan derivative;
   a gelling agent; and
   glyoxal treated hydroxyethyl cellulose (HEC), wherein the pharmaceutical composition is an injectable or bioprintable pharmaceutical hydrogel solution, and
   wherein the pharmaceutical composition sustains the release of the pharmaceutically active agent for at least 30 days by the combined covalent and non-covalent interactions of the cellulose nanocrystal or cellulose nanofiber and the chitosan or chitosan derivate, and the HEC and the chitosan or chitosan derivative, wherein the non-covalent interaction of the cellulose nanocrystal or cellulose nanofiber and the chitosan or chitosan derivate comprises hydrogen bonding, and wherein the covalent interaction of glyoxal molecules from the HEC and the chitosan or chitosan derivative comprises a C=N bond.

2. The pharmaceutical composition of claim 1, wherein the gelling agent is selected from the group consisting of β-glycerophosphate, glycerol and mannitol.

3. The pharmaceutical composition of claim 1, wherein the pharmaceutical composition further comprises one or more compounds selected from the group consisting of: inorganic phosphate salt, glycerol, mannitol, m-cresol and benzyl alcohol.

4. The pharmaceutical composition of claim 1, wherein the pharmaceutical composition is suitable for subcutaneous injection, intramuscular (IM) injection, or intraosseous injection.

5. The pharmaceutical composition of claim 1, wherein the pharmaceutical composition is for treating a bone disorder, wherein the bone disorder is either osteoporosis or a bone disorder that is not osteoporosis.

6. The pharmaceutical composition of claim 1, wherein the pharmaceutical composition is for treating Paget's disease.

7. The pharmaceutical composition of claim 1, wherein the pharmaceutical composition is for treating a disorder through a regenerative medicine.

8. The pharmaceutical composition of claim 1, the composition further comprising a stem cell, wherein the stem cell is encapsulated in or seeded on the thermogelling biocompatible polymer.

9. The pharmaceutical composition of claim 1, wherein the pharmaceutical composition is configured as a bioink suitable for 3D printing.

10. The pharmaceutical composition of claim 9, wherein the bioink comprises one or more of the following properties:
    a viscosity of less than about 800 cP;
    syringeability through a 16-25 gauge needle at room temperature;
    pH of about 6.5 to about 7.5;
    osmolarity of about 260 to about 400 mOsm/kg;
    a yield stress of less than about 600 Pa; and/or
    a storage modulus recovery of at least 90% from its initial storage modulus.

11. The pharmaceutical composition of claim 9, wherein the bioink comprises one or more of the following properties:
    gelation time of less than about one minute; and/or
    post-gelling compression force of about 10 to about 400 kPa; and/or
    supportive of greater than 80% cell viability.

12. The pharmaceutical composition of claim 9, wherein the bioink has a viscosity of less than about 800 cP and/or is syringeable through a 16-25 gauge needle at room temperature.

13. A method of treating a bone disorder comprising administering a therapeutically effective amount of the pharmaceutical composition of claim 1 to a subject in need thereof.

14. The method of claim 13, wherein the administering comprises subcutaneous, intramuscular, or intraosseous injection of the pharmaceutical composition.

15. The method of claim 13, wherein the bone disorder is osteoporosis.

16. A method of treating Paget's disease A comprising administering a therapeutically effective amount of the pharmaceutical composition of claim 1 to a subject in need thereof.

17. The pharmaceutical composition of claim 1, wherein the pharmaceutically active agent comprises a teriparatide, or a pharmaceutically acceptable salt of a teriparatide.

* * * * *